US007947265B2

(12) United States Patent
Galipeau et al.

(10) Patent No.: US 7,947,265 B2
(45) Date of Patent: May 24, 2011

(54) FUSION PROTEINS AND METHODS FOR MODULATION OF IMMUNE RESPONSE

(75) Inventors: Jacques Galipeau, Town of Mount Royal (CA); Moutih Rafei, St. Laurent (CA)

(73) Assignee: McGill University, Montreal, Quebec (CA)

(*) Notice: Subject to any disclaimer, the term of this patent is extended or adjusted under 35 U.S.C. 154(b) by 0 days.

(21) Appl. No.: 12/375,730

(22) PCT Filed: Aug. 2, 2007

(86) PCT No.: PCT/CA2007/001356
§ 371 (c)(1),
(2), (4) Date: Jul. 29, 2009

(87) PCT Pub. No.: WO2008/014612
PCT Pub. Date: Feb. 7, 2008

(65) Prior Publication Data
US 2010/0021421 A1    Jan. 28, 2010

Related U.S. Application Data

(60) Provisional application No. 60/821,194, filed on Aug. 2, 2006.

(51) Int. Cl.
*A61K 38/19*    (2006.01)
*A61K 38/20*    (2006.01)
(52) U.S. Cl. .................. 424/85.1; 424/85.2; 514/21.2
(58) Field of Classification Search .................. None
See application file for complete search history.

(56) References Cited

FOREIGN PATENT DOCUMENTS
WO    WO03/035105 A2    5/2003

OTHER PUBLICATIONS

Rafei et al (2007) Blood, vol. 109, No. 5, pp. 2234-2242.*
Dranoff G. et al. Vaccination with irradiated tumor cells engineered to secrete murine granulocyte-macrophage colony-stimulating factor stimulates potent, specific, and long-lasting anti-tumor immunity. Proceedings of the National Academy of Sciences. 90: 3539-43 (1993).
Irvine KR, Rao JB, Rosenberg SA, Restifo NP. Cytokine enhancement of DNA immunization leads to effective treatment of established pulmonary metastases. Journal of Immunology. 156: 238-45 (1996).
Gillies, Stephen et al. Bi-functional cytokine fusion proteins for gene therapy and antibody-targeted treatment of cancer. Cancer Immunology Immunotherapy. 51: 449-460 (2002).
Stagg J., Wu JH, Bougamin N., Galipeau J. Granulocyte-macrophage colony stimulating factor and interleukin-2 fusion cDNA for cancer gene therapy. Cancer Research. 64: 8795-99 (2004).
Waldmann TA, Tagaya Y. The multifaced regulation of interleukin-15 expression and the role of this cytokine in NK cell differentiation and host response to intracellular pathogens. Annual Reviews in Immunology. 17: 19-49 (1999).
Tagaya Y., Bamford RN, DeFilippis AP, Waldmann TA. IL15: a pleotropic cytokine with diverse receptor/signalling pathways whose expression in controlled at multiple levels. Immunity. 4: 329-36 (1996).
Fehniger TA, Caliguiri MA. Interleukin 15: biology and relevance to human diseases. Blood. 97: 14-32 (2001).
Mrozek E., Anderson P, Caliguiri MA. Role of interleukin-15 in the development of CD56+ natural killer cells from CD34+ hematopoietic progenitor cells. Blood. 87: 2632-40 (1996).
Ohteki T., et al. The transcription factor interferon regulatory factor 1 (IRF-1) is important during the maturation of natural killer 1.1+ T-cell receptor-alpha/beta+ (NK1+T) cells, natural killer cells, and intestinal intraepithelial T cells. Journal of Experimental Medicine. 187: 967-72 (1998).
Fehniger TA et al. Differential cytokine and chemokine gene expression by human NK cells following activation with IL-18 or IL-15 in combination with IL-12: implications for the innate immune response. Journal of Immunology. 162: 4511-20 (1999).
Atedzoe BN, Ahmand A., Menezes J. Enhancement of natural killer cell cytotoxicity by the human herpes-7 via IL-15 induction. *Journal of Immunology*. 159: 4966-72 (1997).
Angiolillo AL, Kanegane H, Sgadari C, Reaman GH, Tosato G. Interleukin-15 promotes angiogenesis in vivo. *Biochemical Biophysical Research Communication*. 233: 231-7 (1997).
Estess P, Nandi A, Mohamadzadeh M, Siegelman MH. Interleukin 15 induces endothelial hyaluronan expression in vitro and promotes activated T cell extravasation through a CD44-dependent pathway in vivo. *Journal of Experimental Medicine*. 190: 9-19 (1999).
Kisselva T., Bhattacharya S., Braunstein J., Schindler CW. Signalling through the JAK/STAT pathway, recent advances and future challenges. *Gene*. 285: 1-24 (2002).
Bromberg J., Darnell JE. The role of STATs in transcriptional control and their impact on cellular function. *Oncogene*. 19: 2468-73 (2000).
Smithgall TE et al. Control of myeloid differentiation and survival by Stats. *Oncogene*. 19: 2612-2618 (2000).
Catlett-Falcone R. et al. Constitutive activation of STAT3 signalling confers resistance to apoptosis in human U266 myeloma cells. *Immunity*. 10: 105-15 (1999).
Niu G. et al. Roles of activated Src and STAT3 signalling in melanoma tumor cell growth. *Oncogene*. 21: 7001-10 (2002).
Wang T. et al. Regulation of the innate and adaptive immune responses by Stat-3 signalling in tumor cells. *Nature Medicine*. 10: 48-54 (2003).
Kortylwski M et al. Inhibiting Stat3 signalling in the hematopoietic system elicits multicomponent antitumor immunity. *Nature Medicine*. 11: 1314-21 (2005). Lorenzen I, Dingley AJ, Jacques Y, Grotzinger J. The Structure of the Interleukin-15α Receptor and Its Implications for Ligand Binding. *Journal of Biological Chemistry*. 281: 6642-6647 (2006).
Jérôme Bernard, et al. Identification of an Interleukin-15α Receptor-binding Site on Human Interleukin-15. *Journal of Biological Chemistry*. 279: 24313-22, (2004).
Stauber DJ, Debler EW, Horton PA, Smith KA, Wilson IA. Crystal structure of the IL-2 signalling complex: Paradigm for a heterotrimeric cytokine receptor. *Proceeding National Academy of Science*. 103: 2788-2793 (2006).
Sainathan SK et al. PEGylated murine Granulocyte-macrophage colony-stimulating factor: production, purification, and characterization. *Protein Expression & Purification*. 44: 94-103 (2005).

(Continued)

*Primary Examiner* — Prema Mertz
(74) *Attorney, Agent, or Firm* — Bereskin & Parr LLP/S.E.N.C.R.L., s.r.l.; Micheline Gravelle

(57) ABSTRACT

A fusion protein comprising GM-CSF and IL-15 is described. The fusion protein has unexpected immune suppressive properties and is useful in a variety of therapeutic applications.

3 Claims, 17 Drawing Sheets

OTHER PUBLICATIONS

Figure 1:
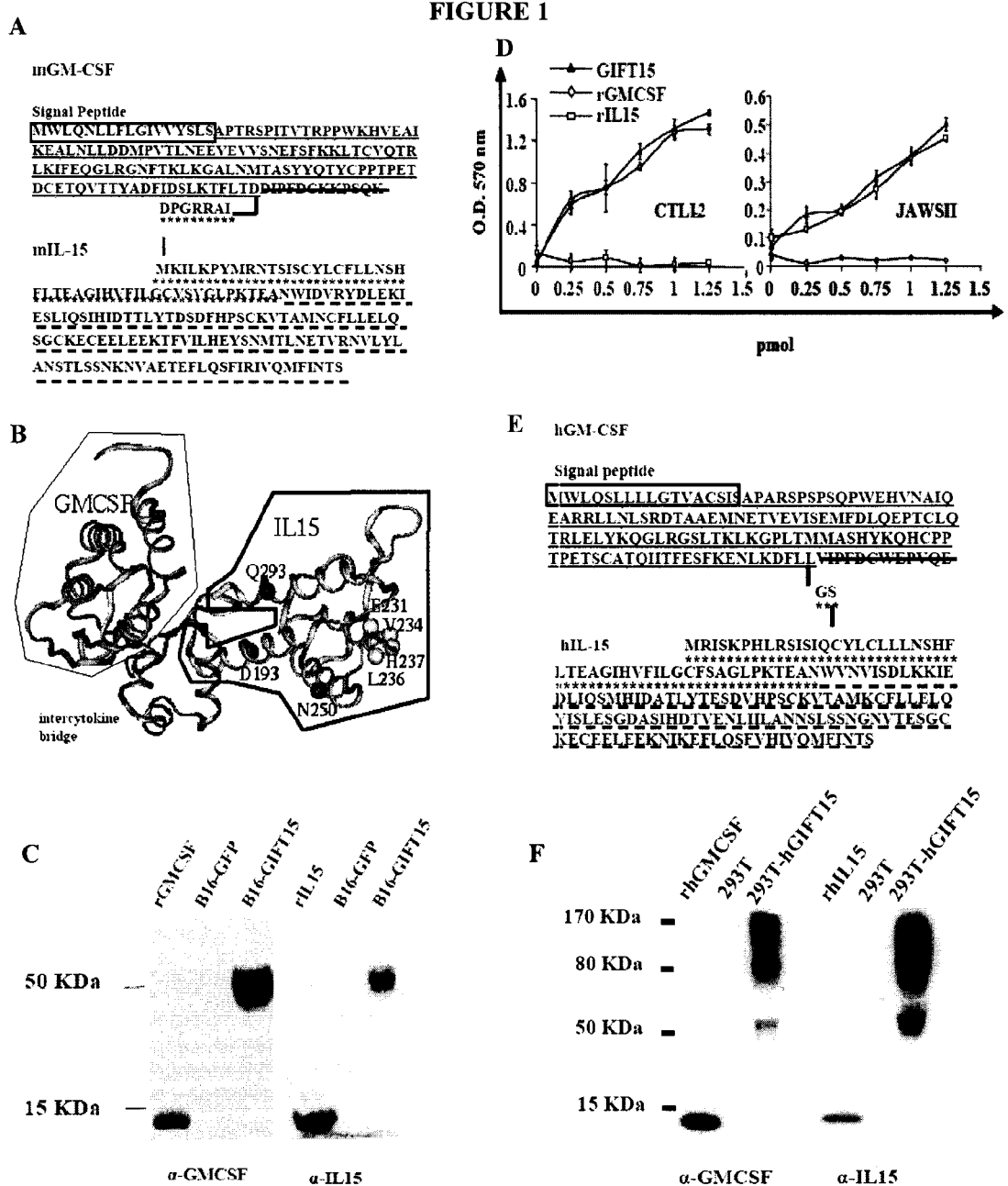

Burgess AW, Metcalf D. Serum half-life and organ distribution of radiolabeled colony stimulating factor in mice. *Experimental Hematology*. 5: 456-64 (1977).

Pettit DK, et al. Structure-function studies of interleukin 15 using site-specific mutagenesis, polyethylene glycol conjugation, and homology modeling. *Journal of Biological Chemistry*. 272: 2312-8 (1997).

Mosmman TR, Coffman RL. Heterogeneity of cytokine secretion patterns and functions of helper T cells. *Advances in Immunology*. 46: 111-47 (1989).

Ulett GC, Ketheesan N, Hirst RG. Cytokine gene expression in innately susceptible BALB/c mice and relatively resistant C57Bl/6 mice during infection with virulent *Burkholderia pseudomallei*. *Infection and Immunity*. 68: 2034-42 (2000).

Wahl S.M., Wen J., Moutsopoulos NM (2006). The kiss of death: interrupted by NK-cell close encounters of another kind. *Trends in Immunology*. 4: 161-4 (2006).

Perri SR, et al. Plasminogen kringle 5-engineered glioma cells block migration of tumor-associated macrophages and suppress tumor vascularization and progression. *Cancer Research*. 65: 8359-65 (2005).

Hoontrakoon, R. et al. "Interleukin-15 Inhibits Spontaneous Apoptosis in Human Eosinophils via Autocrine Production of Granulocyte Macrophage-Colony Stimulating Factor and Nuclear Factor-kB Activation", Am. J. Respir. Cell Mol. Biol. 2002, vol. 26, p. 404-412. ISSN 1044-1549.

Raza, K. et al. "Synovial fluid leukocyte apoptosis is inhibited in patients with very early rheumatoid arthritis". Arthritis Research & Therapy. Jul. 2006, vol. 8, No. 4, R120. ISSN 1478-6362.

Valdembri, D. et al. "In vivo activation of JAK2/STAT-3 pathway during angiogenesis induced by GM-CSF". FASEB J. Feb. 2002, vol. 16, No. 2, p. 225-7. ISSN 1530-6860.

\* cited by examiner

A  Conditionned-media only

B  Soluble factor

C  Neutralization assay using conditioned-media

A

B

A

B

SEQUENCE LISTING

```
<160> NUMBER OF SEQ ID NOS: 4

<210> SEQ ID NO 1
<211> LENGTH: 900
<212> TYPE: DNA
<213> ORGANISM: Murine
<220> FEATURE:
<221> NAME/KEY: CDS
<222> LOCATION: (1)..(900)

<400> SEQUENCE: 1 atg tgg ctg cag aat tta ctt ttc ctg ggc att gtg gtc tac agc ctc        48
Met Trp Leu Gln Asn Leu Leu Phe Leu Gly Ile Val Val Tyr Ser Leu
1               5                   10                  15 tca gca ccc acc cgc tca ccc atc act gtc acc cgg cct tgg aag cat        96
Ser Ala Pro Thr Arg Ser Pro Ile Thr Val Thr Arg Pro Trp Lys His
                20                  25                  30 gta gag gcc atc aaa gaa gcc ctg aac ctc ctg gat gac atg cct gtc       144
Val Glu Ala Ile Lys Glu Ala Leu Asn Leu Leu Asp Asp Met Pro Val
            35                  40                  45 acg ttg aat gaa gag gta gaa gtc gtc tct aac gag ttc tcc ttc aag       192
Thr Leu Asn Glu Glu Val Glu Val Val Ser Asn Glu Phe Ser Phe Lys
        50                  55                  60 aag cta aca tgt gtg cag acc cgc ctg aag ata ttc gag cag ggt cta       240
Lys Leu Thr Cys Val Gln Thr Arg Leu Lys Ile Phe Glu Gln Gly Leu
65                  70                  75                  80 cgg ggc aat ttc acc aaa ctc aag ggc gcc ttg aac atg aca gcc agc       288
Arg Gly Asn Phe Thr Lys Leu Lys Gly Ala Leu Asn Met Thr Ala Ser
```

|  |  |  |  |  |  |  |  |  |  |  |  |  |  |  |  |  |
|---|---|---|---|---|---|---|---|---|---|---|---|---|---|---|---|---|
|  |  |  | 85 |  |  |  | 90 |  |  |  | 95 |  |  |  |  |  |
| tac | tac | cag | aca | tac | tgc | ccc | cca | act | ccg | gaa | acg | gac | tgt | gaa | aca | 336 |
| Tyr | Tyr | Gln | Thr | Tyr | Cys | Pro | Pro | Thr | Pro | Glu | Thr | Asp | Cys | Glu | Thr |  |
|  |  |  | 100 |  |  |  | 105 |  |  |  | 110 |  |  |  |  |  |
| caa | gtt | acc | acc | tat | gcg | gat | ttc | ata | gac | agc | ctt | aaa | acc | ttt | ctg | 384 |
| Gln | Val | Thr | Thr | Tyr | Ala | Asp | Phe | Ile | Asp | Ser | Leu | Lys | Thr | Phe | Leu |  |
|  |  |  | 115 |  |  |  | 120 |  |  |  | 125 |  |  |  |  |  |
| act | gat | gat | ccc | ggt | agg | agg | gcc | atc | atg | aaa | att | ttg | aaa | cca | tat | 432 |
| Thr | Asp | Asp | Pro | Gly | Arg | Arg | Ala | Ile | Met | Lys | Ile | Leu | Lys | Pro | Tyr |  |
|  |  | 130 |  |  |  | 135 |  |  |  | 140 |  |  |  |  |  |  |
| atg | agg | aat | aca | tcc | atc | tcg | tgc | tac | ttg | tgt | ttc | ctt | cta | aac | agt | 480 |
| Met | Arg | Asn | Thr | Ser | Ile | Ser | Cys | Tyr | Leu | Cys | Phe | Leu | Leu | Asn | Ser |  |
| 145 |  |  |  | 150 |  |  |  | 155 |  |  |  | 160 |  |  |  |  |
| cac | ttt | tta | act | gag | gct | ggc | att | cat | gtc | ttc | att | ttg | ggc | tgt | gtc | 528 |
| His | Phe | Leu | Thr | Glu | Ala | Gly | Ile | His | Val | Phe | Ile | Leu | Gly | Cys | Val |  |
|  |  |  |  | 165 |  |  |  | 170 |  |  |  | 175 |  |  |  |  |
| agt | gta | ggt | ctc | cct | aaa | aca | gag | gcc | aac | tgg | ata | gat | gta | aga | tat | 576 |
| Ser | Val | Gly | Leu | Pro | Lys | Thr | Glu | Ala | Asn | Trp | Ile | Asp | Val | Arg | Tyr |  |
|  |  |  | 180 |  |  |  | 185 |  |  |  | 190 |  |  |  |  |  |
| gac | ctg | gag | aaa | att | gaa | agc | ctt | att | caa | tct | att | cat | att | gac | acc | 624 |
| Asp | Leu | Glu | Lys | Ile | Glu | Ser | Leu | Ile | Gln | Ser | Ile | His | Ile | Asp | Thr |  |
|  |  | 195 |  |  |  | 200 |  |  |  | 205 |  |  |  |  |  |  |
| act | tta | tac | act | gac | agt | gac | ttt | cat | ccc | agt | tgc | aaa | gtt | act | gca | 672 |
| Thr | Leu | Tyr | Thr | Asp | Ser | Asp | Phe | His | Pro | Ser | Cys | Lys | Val | Thr | Ala |  |
| 210 |  |  |  | 215 |  |  |  | 220 |  |  |  |  |  |  |  |  |
| atg | aac | tgc | ttt | ctc | ctg | gaa | ttg | cag | gtt | att | tta | cat | gag | tac | agt | 720 |
| Met | Asn | Cys | Phe | Leu | Leu | Glu | Leu | Gln | Val | Ile | Leu | His | Glu | Tyr | Ser |  |
| 225 |  |  |  | 230 |  |  |  | 235 |  |  |  | 240 |  |  |  |  |
| aac | atg | act | ctt | aat | gaa | aca | gta | aga | aac | gtg | ctc | tac | ctt | gca | aac | 768 |
| Asn | Met | Thr | Leu | Asn | Glu | Thr | Val | Arg | Asn | Val | Leu | Tyr | Leu | Ala | Asn |  |
|  |  |  |  | 245 |  |  |  | 250 |  |  |  | 255 |  |  |  |  |
| agc | act | ctg | tct | tct | aac | aag | aat | gta | gca | gaa | tct | ggc | tgc | aag | gaa | 816 |
| Ser | Thr | Leu | Ser | Ser | Asn | Lys | Asn | Val | Ala | Glu | Ser | Gly | Cys | Lys | Glu |  |
|  |  |  | 260 |  |  |  | 265 |  |  |  | 270 |  |  |  |  |  |
| tgt | gag | gag | ctg | gag | gag | aaa | acc | ttc | aca | gag | ttt | ttg | caa | agc | ttt | 864 |
| Cys | Glu | Glu | Leu | Glu | Glu | Lys | Thr | Phe | Thr | Glu | Phe | Leu | Gln | Ser | Phe |  |
|  | 275 |  |  |  | 280 |  |  |  | 285 |  |  |  |  |  |  |  |
| ata | cgc | att | gtc | caa | atg | ttc | atc | aac | acg | tcc | tga |  |  |  |  | 900 |
| Ile | Arg | Ile | Val | Gln | Met | Phe | Ile | Asn | Thr | Ser |  |  |  |  |  |  |
| 290 |  |  |  | 295 |  |  |  |  |  |  |  |  |  |  |  |  |

<210> SEQ ID NO 2
<211> LENGTH: 299
<212> TYPE: PRT
<213> ORGANISM: Murine

<400> SEQUENCE: 2

Met Trp Leu Gln Asn Leu Leu Phe Leu Gly Ile Val Val Tyr Ser Leu
1               5                   10                  15

Ser Ala Pro Thr Arg Ser Pro Ile Thr Val Thr Arg Pro Trp Lys His
                20                  25                  30

Val Glu Ala Ile Lys Glu Ala Leu Asn Leu Leu Asp Asp Met Pro Val
            35                  40                  45

Thr Leu Asn Glu Glu Val Glu Val Val Ser Asn Glu Phe Ser Phe Lys
        50                  55                  60

Lys Leu Thr Cys Val Gln Thr Arg Leu Lys Ile Phe Glu Gln Gly Leu
65                  70                  75                  80

Arg Gly Asn Phe Thr Lys Leu Lys Gly Ala Leu Asn Met Thr Ala Ser
                85                  90                  95

```
Tyr Tyr Gln Thr Tyr Cys Pro Pro Thr Pro Glu Thr Asp Cys Glu Thr
            100                 105                 110

Gln Val Thr Thr Tyr Ala Asp Phe Ile Asp Ser Leu Lys Thr Phe Leu
        115                 120                 125

Thr Asp Asp Pro Gly Arg Arg Ala Ile Met Lys Ile Leu Lys Pro Tyr
    130                 135                 140

Met Arg Asn Thr Ser Ile Ser Cys Tyr Leu Cys Phe Leu Leu Asn Ser
145                 150                 155                 160

His Phe Leu Thr Glu Ala Gly Ile His Val Phe Ile Leu Gly Cys Val
                165                 170                 175

Ser Val Gly Leu Pro Lys Thr Glu Ala Asn Trp Ile Asp Val Arg Tyr
            180                 185                 190

Asp Leu Glu Lys Ile Glu Ser Leu Ile Gln Ser Ile His Ile Asp Thr
        195                 200                 205

Thr Leu Tyr Thr Asp Ser Asp Phe His Pro Ser Cys Lys Val Thr Ala
    210                 215                 220

Met Asn Cys Phe Leu Leu Glu Leu Gln Val Ile Leu His Glu Tyr Ser
225                 230                 235                 240

Asn Met Thr Leu Asn Glu Thr Val Arg Asn Val Leu Tyr Leu Ala Asn
                245                 250                 255

Ser Thr Leu Ser Ser Asn Lys Asn Val Ala Glu Ser Gly Cys Lys Glu
            260                 265                 270

Cys Glu Glu Leu Glu Glu Lys Thr Phe Thr Glu Phe Leu Gln Ser Phe
        275                 280                 285

Ile Arg Ile Val Gln Met Phe Ile Asn Thr Ser
        290                 295

<210> SEQ ID NO 3
<211> LENGTH: 894
<212> TYPE: DNA
<213> ORGANISM: Homo sapiens
<220> FEATURE:
<221> NAME/KEY: CDS
<222> LOCATION: (1)..(894)

<400> SEQUENCE: 3 atg tgg ctg cag agc ctg ctg ctc ttg ggc act gtg gcc tgc agc atc     48
Met Trp Leu Gln Ser Leu Leu Leu Leu Gly Thr Val Ala Cys Ser Ile
1               5                   10                  15 tct gca ccc gcc cgc tcg ccc agc ccc agc acg cag ccc tgg gag cat     96
Ser Ala Pro Ala Arg Ser Pro Ser Pro Ser Thr Gln Pro Trp Glu His
                20                  25                  30 gtg aat gcc atc cag gag gcc cgg cgt ctc ctg aac ctg agt aga gac    144
Val Asn Ala Ile Gln Glu Ala Arg Arg Leu Leu Asn Leu Ser Arg Asp
            35                  40                  45 act gct gct gag atg aat gaa aca gta gaa gtc atc tca gaa atg ttt    192
Thr Ala Ala Glu Met Asn Glu Thr Val Glu Val Ile Ser Glu Met Phe
        50                  55                  60 gac ctc cag gag ccg acc tgc cta cag acc cgc ctg gag ctg tac aag    240
Asp Leu Gln Glu Pro Thr Cys Leu Gln Thr Arg Leu Glu Leu Tyr Lys
65                  70                  75                  80 cag ggc ctg cgg ggc agc ctc acc aag ctc aag ggc ccc ttg acc atg    288
Gln Gly Leu Arg Gly Ser Leu Thr Lys Leu Lys Gly Pro Leu Thr Met
                85                  90                  95 atg gcc agc cac tac aag cag cac tgc cct cca acc ccg gaa act tcc    336
Met Ala Ser His Tyr Lys Gln His Cys Pro Pro Thr Pro Glu Thr Ser
            100                 105                 110 tgt gca acc cag att atc acc ttt gaa agt ttc aaa gag aac ctg aag    384
Cys Ala Thr Gln Ile Ile Thr Phe Glu Ser Phe Lys Glu Asn Leu Lys
```

-continued

```
                       115                 120                     125
gac ttt ctg ctt gtc gga tcc atg cga att tcg aaa cca cat ttg aga        432
Asp Phe Leu Leu Val Gly Ser Met Arg Ile Ser Lys Pro His Leu Arg
    130                 135                 140 agt att tcc atc cag tgc tac ttg tgt tta ctt cta aac agt cat ttt        480
Ser Ile Ser Ile Gln Cys Tyr Leu Cys Leu Leu Leu Asn Ser His Phe
145                 150                 155                 160 cta act gaa gct ggc att cat gtc ttc att ttg ggc tgt ttc agt gca        528
Leu Thr Glu Ala Gly Ile His Val Phe Ile Leu Gly Cys Phe Ser Ala
                165                 170                 175 ggg ctt cct aaa aca gaa gcc aac tgg gtg aat gta ata agt gat ttg        576
Gly Leu Pro Lys Thr Glu Ala Asn Trp Val Asn Val Ile Ser Asp Leu
            180                 185                 190 aaa aaa att gaa gat ctt att caa tct atg cat att gat gct act tta        624
Lys Lys Ile Glu Asp Leu Ile Gln Ser Met His Ile Asp Ala Thr Leu
        195                 200                 205 tat acg gaa agt gat gtt cac ccc agt tgc aaa gta aca gca atg aag        672
Tyr Thr Glu Ser Asp Val His Pro Ser Cys Lys Val Thr Ala Met Lys
    210                 215                 220 tgc ttt ctc ttg gag tta caa gtt att tca ctt gag tcc gga gat gca        720
Cys Phe Leu Leu Glu Leu Gln Val Ile Ser Leu Glu Ser Gly Asp Ala
225                 230                 235                 240 agt att cat gat aca gta gaa aat ctg atc atc cta gca aac aac agt        768
Ser Ile His Asp Thr Val Glu Asn Leu Ile Ile Leu Ala Asn Asn Ser
                245                 250                 255 ttg tct tct aat ggg aat gta aca gaa tct gga tgc aaa gaa tgt gag        816
Leu Ser Ser Asn Gly Asn Val Thr Glu Ser Gly Cys Lys Glu Cys Glu
            260                 265                 270 gaa ctg gag gaa aaa aat att aaa gaa ttt ttg cag agt ttt gta cat        864
Glu Leu Glu Glu Lys Asn Ile Lys Glu Phe Leu Gln Ser Phe Val His
        275                 280                 285 att gtc caa atg ttc atc aac act tct tga                                894
Ile Val Gln Met Phe Ile Asn Thr Ser
    290                 295

<210> SEQ ID NO 4
<211> LENGTH: 297
<212> TYPE: PRT
<213> ORGANISM: Homo sapiens

<400> SEQUENCE: 4

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Gly Ser Met Arg Ile Ser Lys Pro His Leu Arg
    130                 135                 140
```

```
Ser Ile Ser Ile Gln Cys Tyr Leu Cys Leu Leu Leu Asn Ser His Phe
145                 150                 155                 160

Leu Thr Glu Ala Gly Ile His Val Phe Ile Leu Gly Cys Phe Ser Ala
            165                 170                 175

Gly Leu Pro Lys Thr Glu Ala Asn Trp Val Asn Val Ile Ser Asp Leu
            180                 185                 190

Lys Lys Ile Glu Asp Leu Ile Gln Ser Met His Ile Asp Ala Thr Leu
            195                 200                 205

Tyr Thr Glu Ser Asp Val His Pro Ser Cys Lys Val Thr Ala Met Lys
            210                 215                 220

Cys Phe Leu Leu Glu Leu Gln Val Ile Ser Leu Glu Ser Gly Asp Ala
225                 230                 235                 240

Ser Ile His Asp Thr Val Glu Asn Leu Ile Ile Leu Ala Asn Asn Ser
                245                 250                 255

Leu Ser Ser Asn Gly Asn Val Thr Glu Ser Gly Cys Lys Glu Cys Glu
            260                 265                 270

Glu Leu Glu Glu Lys Asn Ile Lys Glu Phe Leu Gln Ser Phe Val His
            275                 280                 285

Ile Val Gln Met Phe Ile Asn Thr Ser
290                 295
```

FUSION PROTEINS AND METHODS FOR MODULATION OF IMMUNE RESPONSE

FIELD OF THE INVENTION

The invention relates to fusion proteins useful in the modulation of immune response.

BACKGROUND OF THE INVENTION

Immune stimulatory cytokines can be exploited to treat human ailments including cancer. Amongst cytokines identified for such use, Granulocyte-Macrophage-Colony Stimulating Factor (GM-CSF) has been under much scrutiny since it acts directly on the adaptive immune system by enhancing antigen presentation as well as costimulation[1,2]. Furthermore, second generation strategies linking innate and adaptive immunity using GM-CSF delivered as a fusion cytokine (fusokine) with other immune stimulatory proteins such as Interleukin-2 (IL-2) and IL-3 have been developed[3,4]. GM-CSF was first described as a growth factor for granulocyte and macrophage progenitor cells. However, GM-CSF is also an important mediator for inflammatory reactions produced by T lymphocytes, macrophages and mast cells present at sites of inflammation[5]. GM-CSF is a strong chemoattractant for neutrophils. It enhances microbicidal activity, phagocytotic activity and cytotoxicity of neutrophils and macrophages. An important feature of GM-CSF is that it greatly enhances the state of antigen presentation on dendritic cells, known to be crucial mediators of acquired immunity. The DNA and protein sequences of GM-CSF have been protected under PCT application WO8600639 and the derived patents.

IL-15 is a pleiotropic cytokine that plays an important role in both the innate and adaptive immune system. IL-15 promotes the activation of neutrophils and macrophages, and is critical to dendritic cell function. In addition, IL-15 is essential to the development, homeostasis, function and survival of natural killer (NK) cells, NK T (NKT) cells and CD8+ T cells. Based on these properties, IL-15 has been proposed as a useful cytokine for immunotherapy. It is currently being investigated in settings of immune deficiency, for the in vitro expansion of T and NK cells, as well as an adjuvant for vaccines[6]. The only stimulatory IL-15 molecule has been described in the form of the cDNA of IL-15 in U.S. Pat. No. 5,552,303.

IL-15 is expressed in several inflammatory disorders, including rheumatoid arthritis, psoriasis, pulmonary inflammatory diseases and diabetes. The beneficial effect of IL-15 neutralisation in autoimmune disease models of psoriasis and diabetes has been proposed in the literature[7]. IL15 antagonists, such as IL-15 "muteins", Fc derivatives, or antibodies directed against IL-15 or IL-15 Receptor (IL-15R) have been developed for immunosuppression[8,9]. U.S. Pat. No. 6,013,480 refers to an antagonist of IL-15 encoded by a DNA of IL-15 mutated in Asp56 or Gln156 via addition, substitution, or deletion that still binds to the IL-15 R α-subunit but no longer to the β or γ-subunits thus preventing any signal transduction. U.S. Pat. No. 6,165,466 describes an IL-15 specific monoclonal antibody directed against the epitopes containing Asp56/Gln156 preventing signal transduction via the IL-15 R. This antibody is protected in its humanized form under U.S. Pat. No. 6,177,079.

IL-2 and IL-15 have pivotal roles in the control of the life and death of lymphocytes. Although their heterotrimeric receptors have two receptor subunits in common, these two cytokines have contrasting roles in adaptive immune responses. The unique role of IL-2 is in the elimination of self-reactive T cells to prevent autoimmunity. By contrast, IL-15 is dedicated to the prolonged maintenance of memory T-cell responses to invading pathogens.

Therefore, both cytokines could affect the immune system as complimentary fusion proteins in the development of novel therapies for malignancy and autoimmune diseases, as well as the design of vaccines against infectious diseases[10].

SUMMARY OF THE INVENTION

The present inventors have prepared a conjugate that comprises Granulocyte-Macrophage-Colony Stimulating Factor (GM-CSF) and interleukin-15 (IL-15) and have surprisingly shown that the conjugate acts as an immune suppressant. This is completely unexpected as both GM-CSF and IL-15 are immune stimulatory molecules.

Consequently, in one aspect, the present invention provides a method of suppressing an immune response comprising administering an effective amount of a GM-CSF and IL-15 conjugate protein, or a nucleic acid sequence encoding a GM-CSF and IL-15 conjugate protein, to an animal in need of such treatment.

In one embodiment, the present invention provides a method of suppressing an immune response to a transplanted organ, tissue or cell comprising administering an effective amount of a GM-CSF or IL-15 conjugate protein or a nucleic acid sequence encoding a GM-CSF or IL-15 conjugate protein to an animal in need thereof.

In another embodiment, the present invention provides a method of preventing or inhibiting an autoimmune disease comprising administering an effective amount of a GM-CSF and IL-15 conjugate protein or a nucleic acid sequence encoding a GM-CSF and IL-15 conjugate protein to an animal in need thereof.

In yet another embodiment, the present invention provides a method of inducing angiogenesis comprising administering an effective amount of a GM-CSF and IL-15 conjugate protein or a nucleic acid sequence encoding a GM-CSF and IL-15 conjugate protein to an animal in need thereof.

The invention also includes novel conjugates comprising GM-CSF and IL-15. As specific embodiment, the novel conjugate has a sequence shown in SEQ ID NOs:1-4 or a homolog or analog thereof.

The invention further includes pharmaceutical compositions comprising GM-CSF and IL-15 conjugate proteins or nucleic acids encoding GM-CSF and IL-15 conjugate proteins for use in suppressing an immune response, inducing angiogenesis, and inhibiting cell death.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

Further features and advantages of the present invention will become apparent from the following detailed description, taken in combination with the appended drawings, in which:

FIG. 1 Structure and function of the recombinant (r) mouse (m) GIFT15 fusokine. (*a*) Schematic representation of the mGIFT15 amino acid (aa) sequence comprising GM-CSF (solid underline), an intercytokine bridge (asterisk), and IL-15 (broken underline). (b) Predicted structural model of mGIFT15 interacting with IL-15Rα, IL2Rβ and IL2Rγ via the aa residues in yellow (E231, V234, and H237), purple (D193 and N250), and red (Q293), respectively. (c) mGIFT15 expression in B16 F0 transduced cancer cells confirmed in a Western blot using antibodies specific for mouse GM-CSF and IL-15. (d) Confirmation of the biological activity of GIFT15 in IL-15 dependent CTLL-2 and GM-CSF dependent JAWSII cell lines. (e) Schematic representation of the human (h) GIFT15 aa sequence comprising GM-CSF (solid underline), an intercytokine bridge (asterisks) and and IL-15 (broken underline); (f) hGIFT15 expression in CHO cells confirmed in a Western blot using antibodies specific for human GM-CSF and IL-15.

Figure 2:
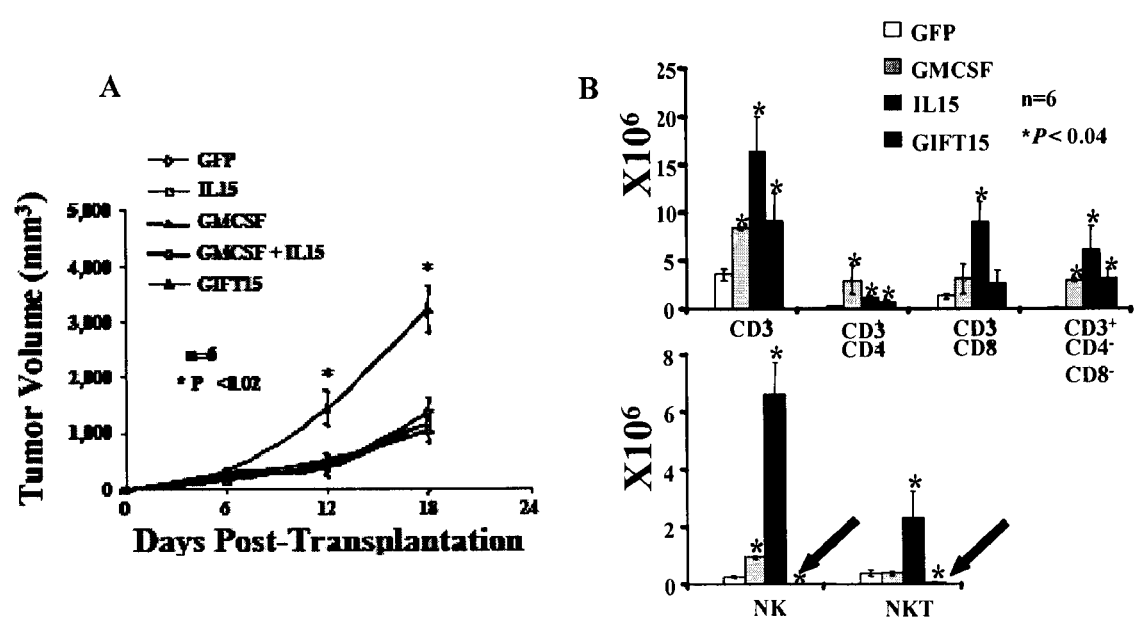

FIG. 2 Immunosuppressive Properties of GIFT15 in a syngeneic model. (a) Increased tumor growth as in vivo effect of GIFT15 in syngeneic immunocompetent C57BI/6 mice inoculated with genetically modified B16F0 cancer cells. (b) Decreased number of NK and NKT cells in the in vitro analysis of tumor infiltrates.

Figure 3:
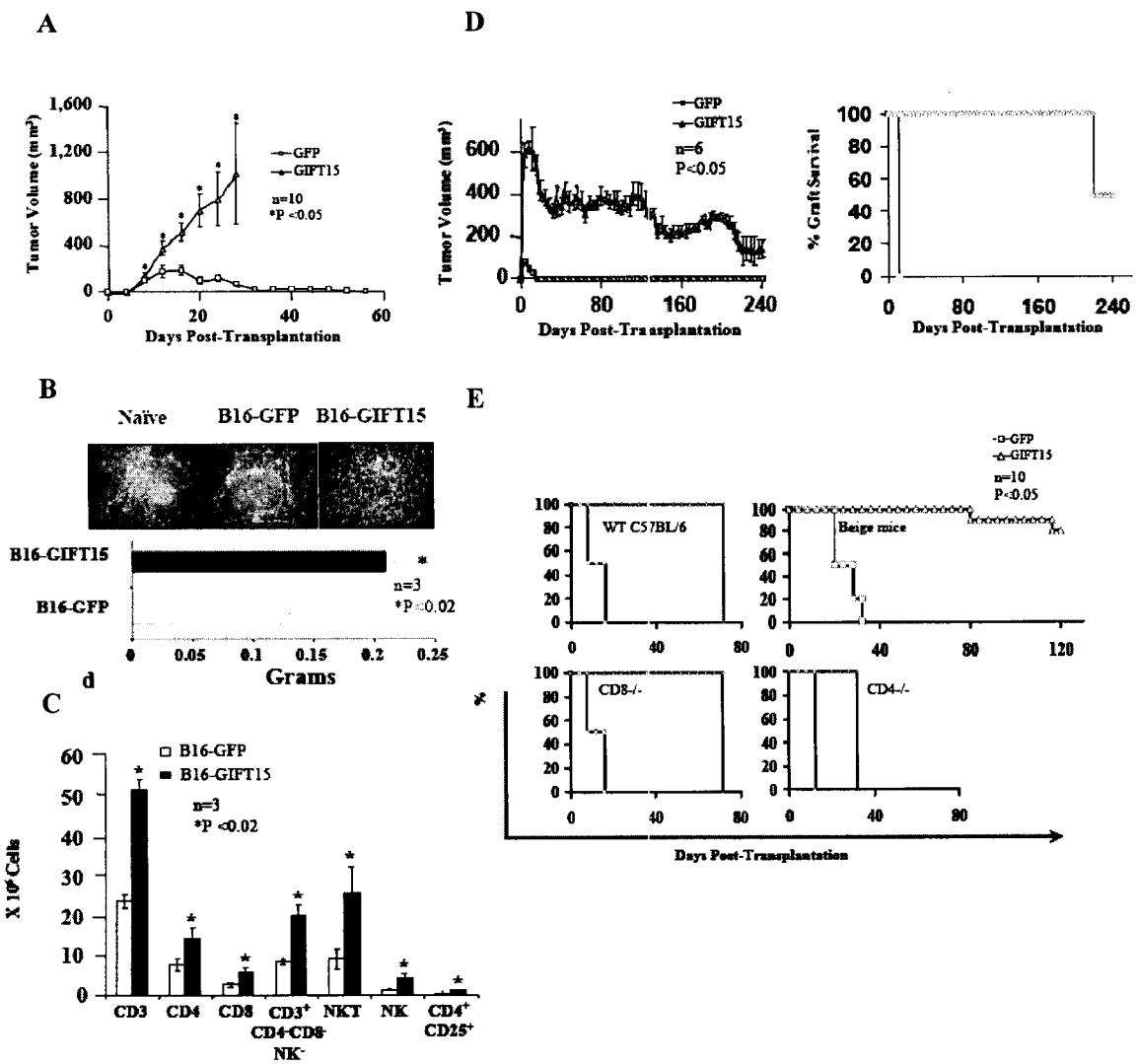

FIG. 3 Allogeneic and xenogeneic transplantation of tumors into immunocompetent mice facilitated by GIFT15. (a) Uninhibited tumor growth of GIFT15 transduced B16F0 cancer cells in allogeneic immunocompetent BALB/c mice. (b) Splenomegaly arising in BALB/c mice described in (a). (c) Increased absolute numbers of T and NK cells in BALB/c mice described in (a) determined by flow cytometry. (d) Tumor growth of GIFT15 transduced human U87GM cancer cells in immunocompetent BALB/c mice and xenograft survival compared to control, i.e. Green Fluorescent Protein (GFP) transduced cancer cells. (e) Survival of xenograft described in (d) in WT C57BI/6, CD4 and CD8 knock-out (KO) mice, and beige mice stressing the importance of CD4 positive cells for the GIFT15 effect in recipients.

Figure 4:
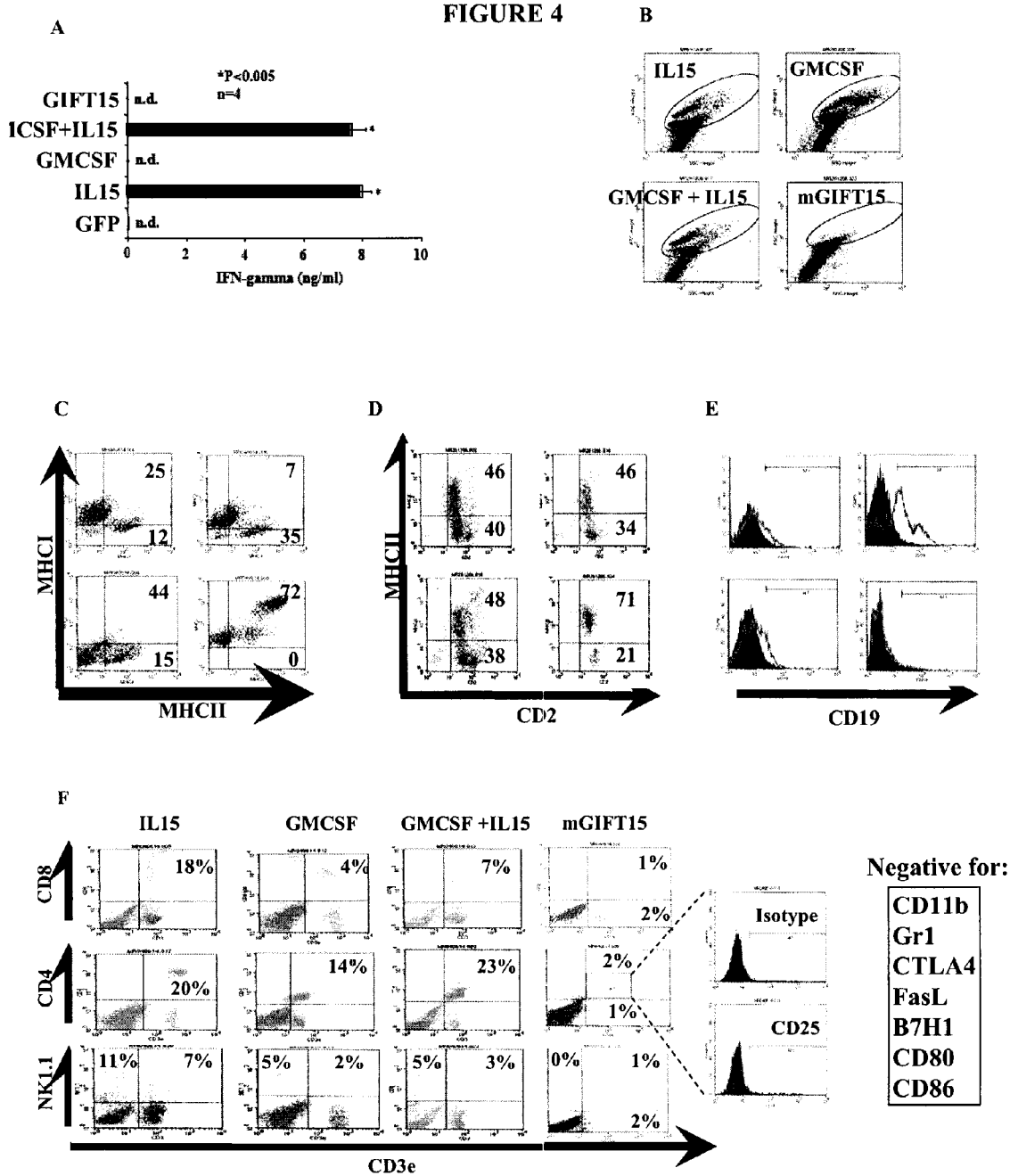

FIG. 4 Phenotypic analysis of cells involved in the GIFT15 induced immunosuppression. (a) IFN-γ secretion by splenocytes activated by rmGM-CSF, rmIL-15, both cytokines or mGIFT15. (b) Schematic presentation of the gates set for the flow cytometry analysis of splenocytes described in (a). (c) Increased MHCI-MHCII co-expression on GIFT15 treated splenocytes described in (a). (d) Increased MHCII-CD2 co-expression on GIFT15 treated splenocytes described in (a). (e) Elimination of B cells as splenocytes described in (d) by CD19 staining. (f) Profiling of splenocytes described in (a) with antibodies for CD3, CD4, CD8, NKT cell markers, CD11b, Gr1, CTLA-4, FasL, B7H1, CD80 and CD86.

Figure 5:
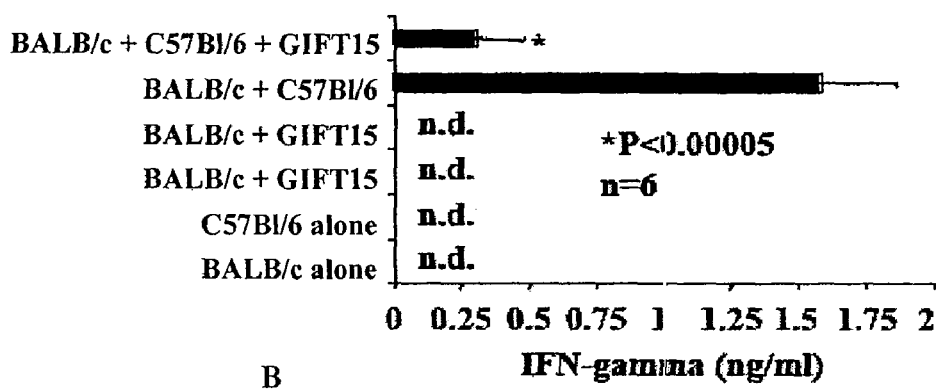
Figure 5:
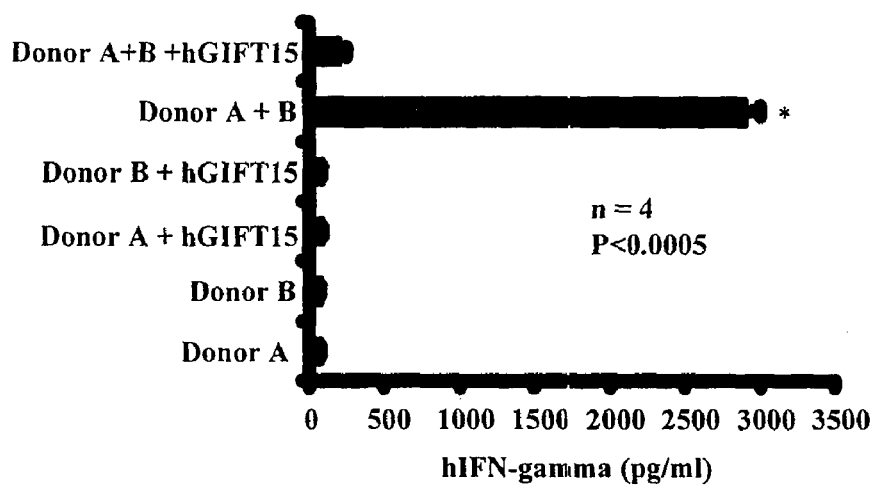
Figure 5:
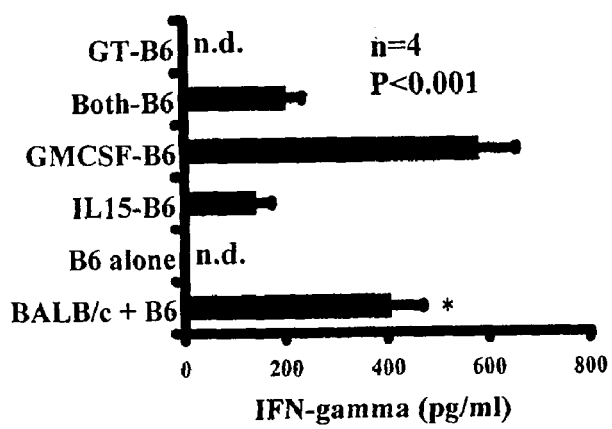

FIG. 5 Effects of mGIFT15 and hGIFT15 in direct and indirect Mixed Lymphocyte Reaction (MLR) assays. (a) IFN-γ secretion in a MLR between equal numbers of splenocytes from BALB/c and C57BI/6 mice in the presence or absence of 180 nM mGIFT15. (b) IFN-γ secretion in a MLR between equal numbers of peripheral blood lymphocytes (PBL) from 2 human donors in the presence or absence of hGIFT15. (c) Indirect immunosuppressive effect of mGIFT15 in a MLR between C57BI/6 (B6) splenocytes pre-treated with mGIFT15 and subsequently added to BALB/c splenocytes in a 1:1 ratio in the absence of mGIFT15.

Figure 6:
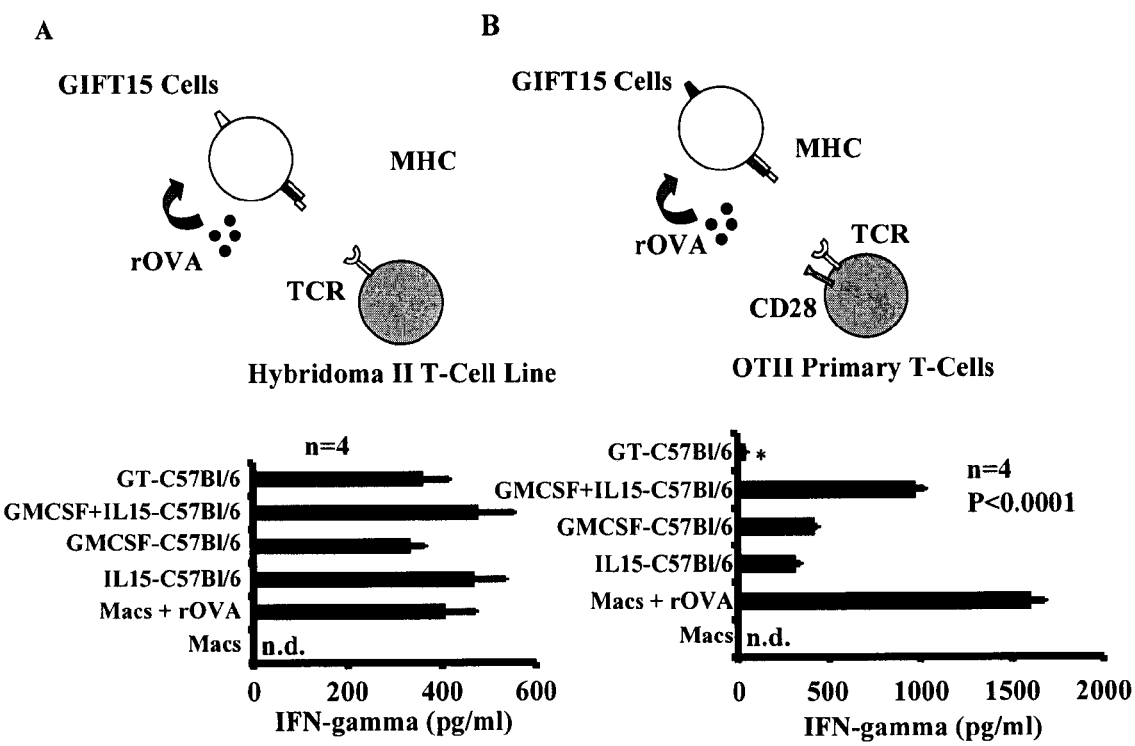

FIG. 6 The indirect effect of GIFT15 on antigen presentation and IFN-γ production in syngeneic in vitro systems. (a) Unhampered antigen presentation by GIFT15 treated C57BI/6 splenocytes to an ovalbumin (OVA) specific MHCII restricted T-cell hybridoma cell line subsequently secreting IFN-γ. (b) Suppression of IFN-γ secretion by primary OTII T-cells in the presence of GIFT15 pre-treated C57BI/6 splenocytes. N.B. The OTII mouse strain is transgenic for a T cell receptor (TCR) recognizing the $OVA_{323-339}$ peptide in the context of MHCII I-$A^b$, i.e. C57BI/6.

Figure 7:
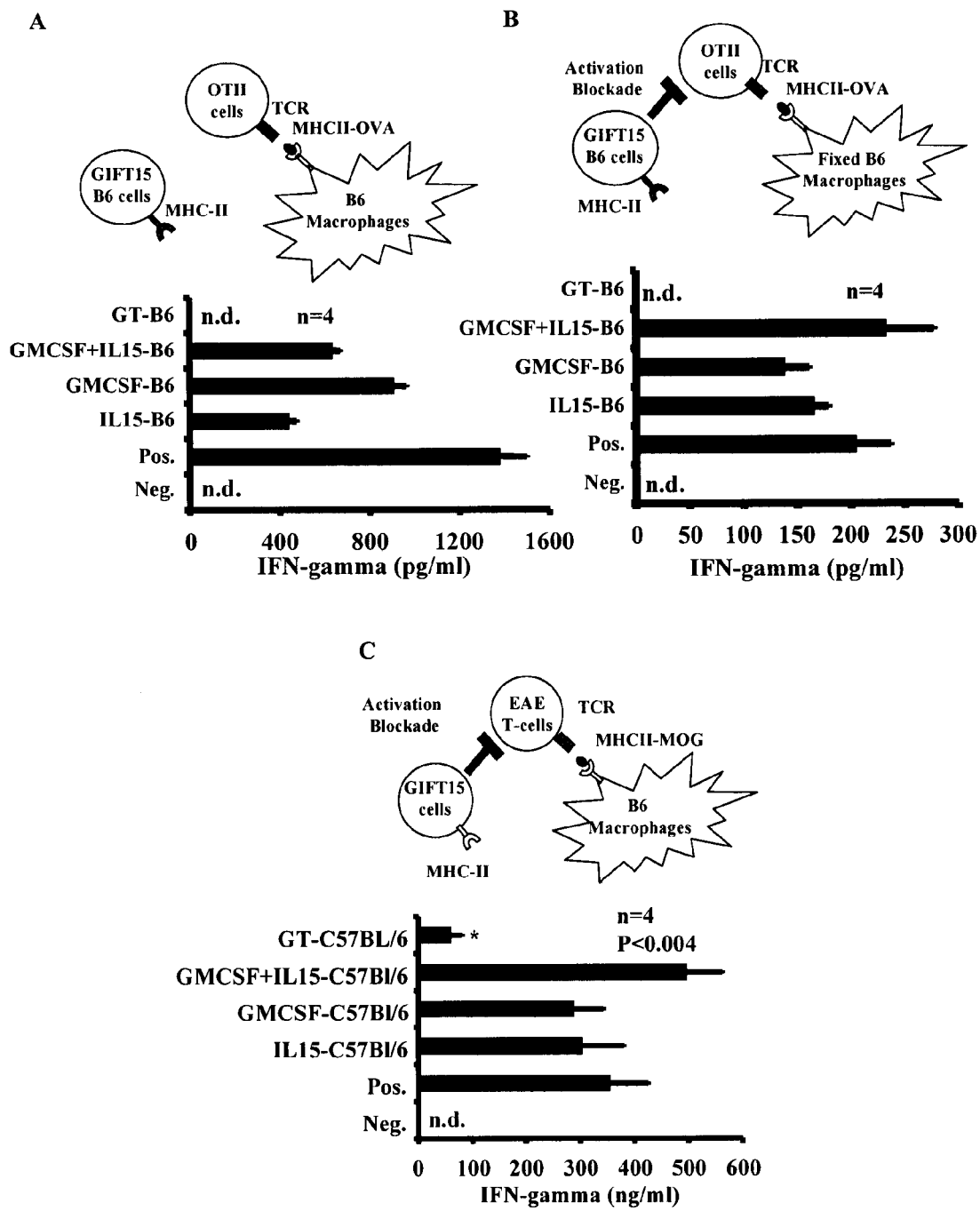

FIG. 7 Inhibition of antigen dependent T cell activation by GIFT15 treated splenocytes as bystander cells and not as antigen presenting cells. (a) Suppression of activation and IFN-γ secretion by OTII T cells recognizing rOVA presented by C57BI/6 peritoneal macrophages in the presence of mGIFT15 treated C57BI/6 splenocytes. (b) Suppression of activation and IFN-γ secretion by OTII T cells recognizing rOVA presented by fixed C57BI/6 peritoneal macrophages in the presence of mGIFT15 treated C57BI/6 splenocytes. (c) Suppression of activation and IFN-γ secretion by $MOG_{35-55}$ specific primary T-cells derived from Myelin Oligodendrocyte Glycoprotein (MOG) induced Experimental Autoimmune Encephalitis (EAE) mice in culture conditions as in (a).

Figure 8:
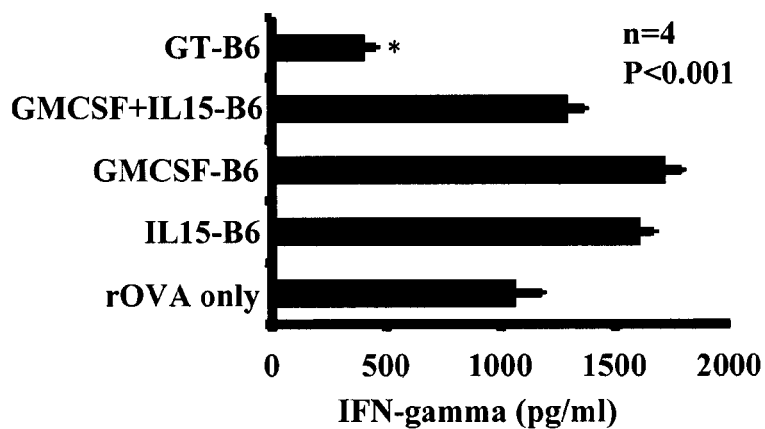
Figure 8:
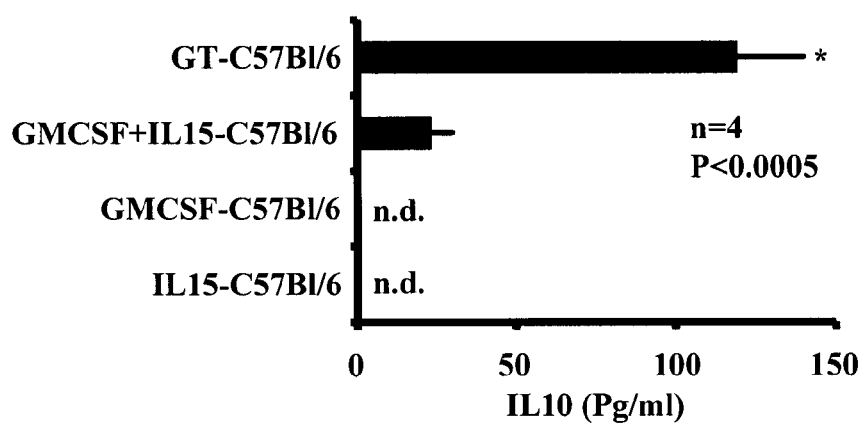
Figure 8:
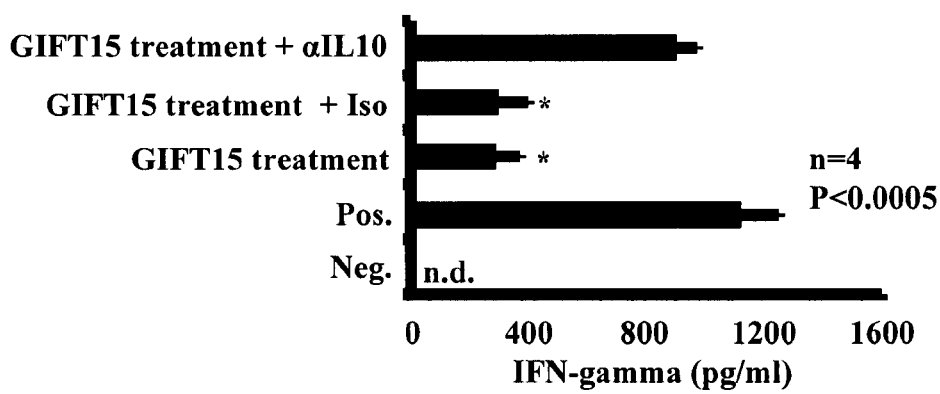

FIG. 8 Partially blocked T cell activation by mGIFT15 through IL10 secretion. (a) mGIFT15 induced suppression based on soluble factors. (b) Identification of IL-10 as the soluble factor involved in mGIFT15 induced immunosuppression by ELISA. (c) Confirmation of IL-10 as the soluble factor involved in mGIFT15 induced immunosuppression by neutralization with an IL-10 specific antibody.

Figure 9:
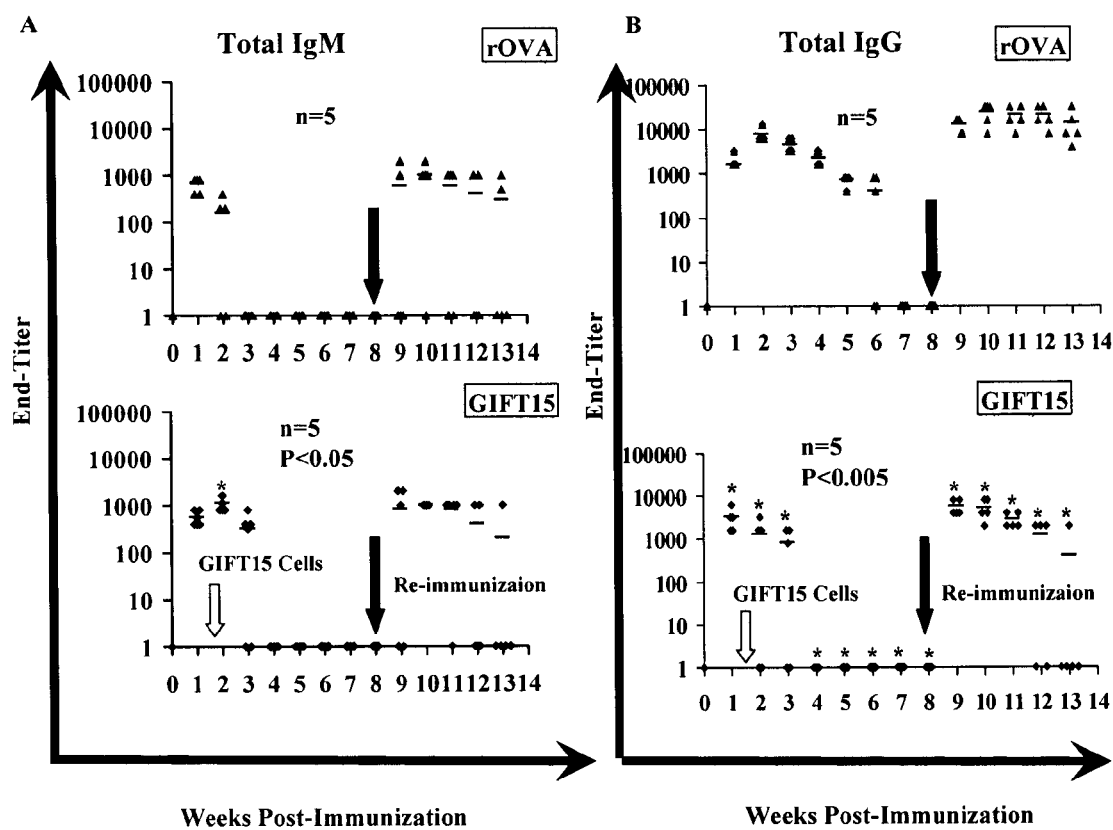

FIG. 9 Suppression of humoral in vivo responses by mGIFT15 by antibody titer analysis. (a) Lack of influence on an OVA directed IgM B cell response by mGIFT15. (b) Induction of transient immunosuppression of the secondary IgG B cell response by mGIFT15.

Figure 10:
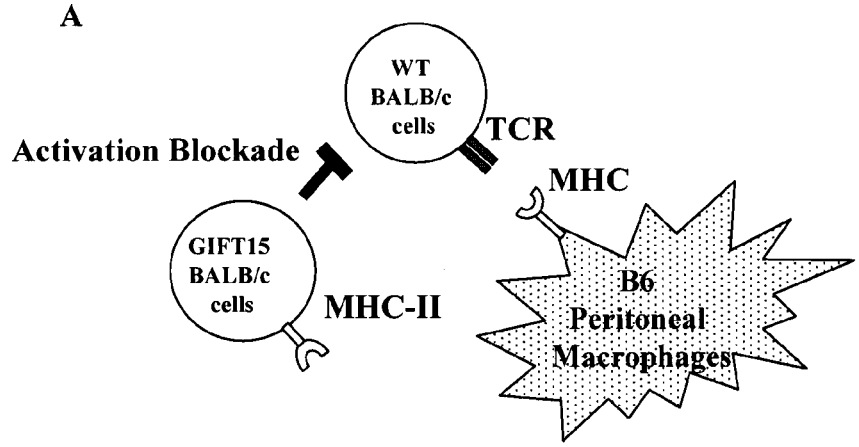
Figure 10:
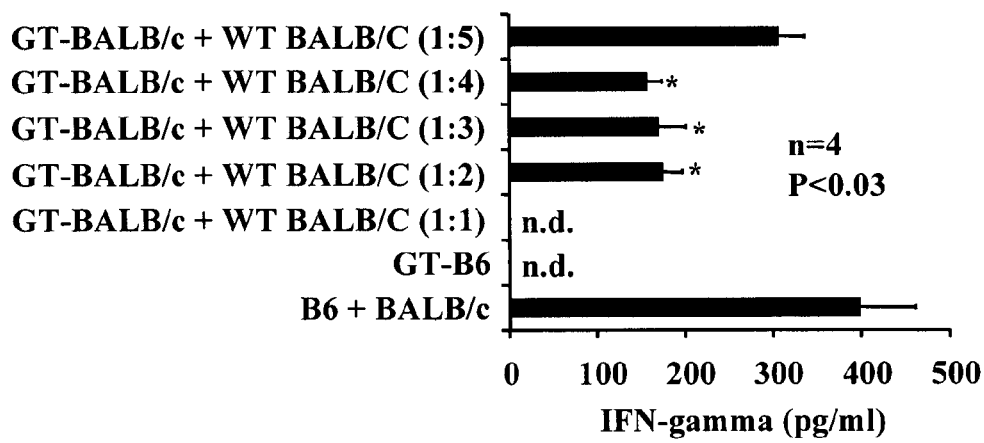
Figure 10:
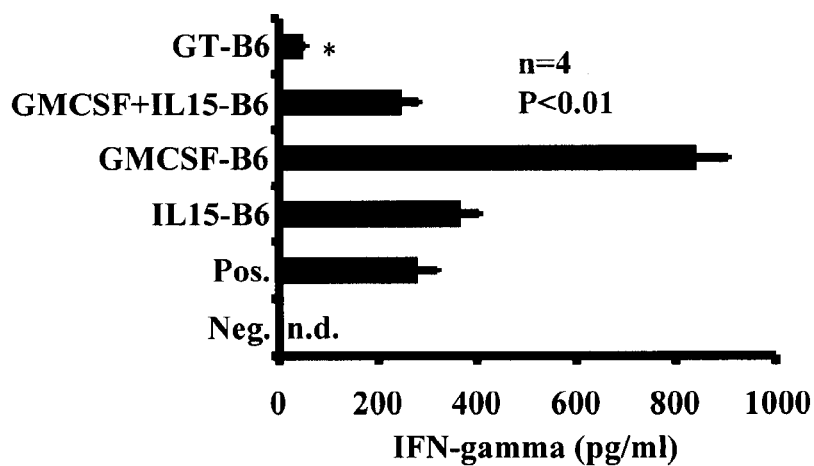

FIG. 10 Syngeneic suppression of allogeneic activation in vitro by mGIFT15 treated BALB/c splenocytes. (a) Preliminary calibration of mGIFT15 immunosuppressive effects of BALB/c splenocytes challenged by allogeneic immunostimulation by C57BI/6 macrophages. (b) The immunosuppressive effect of supernatant from mGIFT15 treated splenocytes added to BALB/c splenocytes cultured in a 1:1 ratio with C57BI/6 macrophages.

Figure 11:
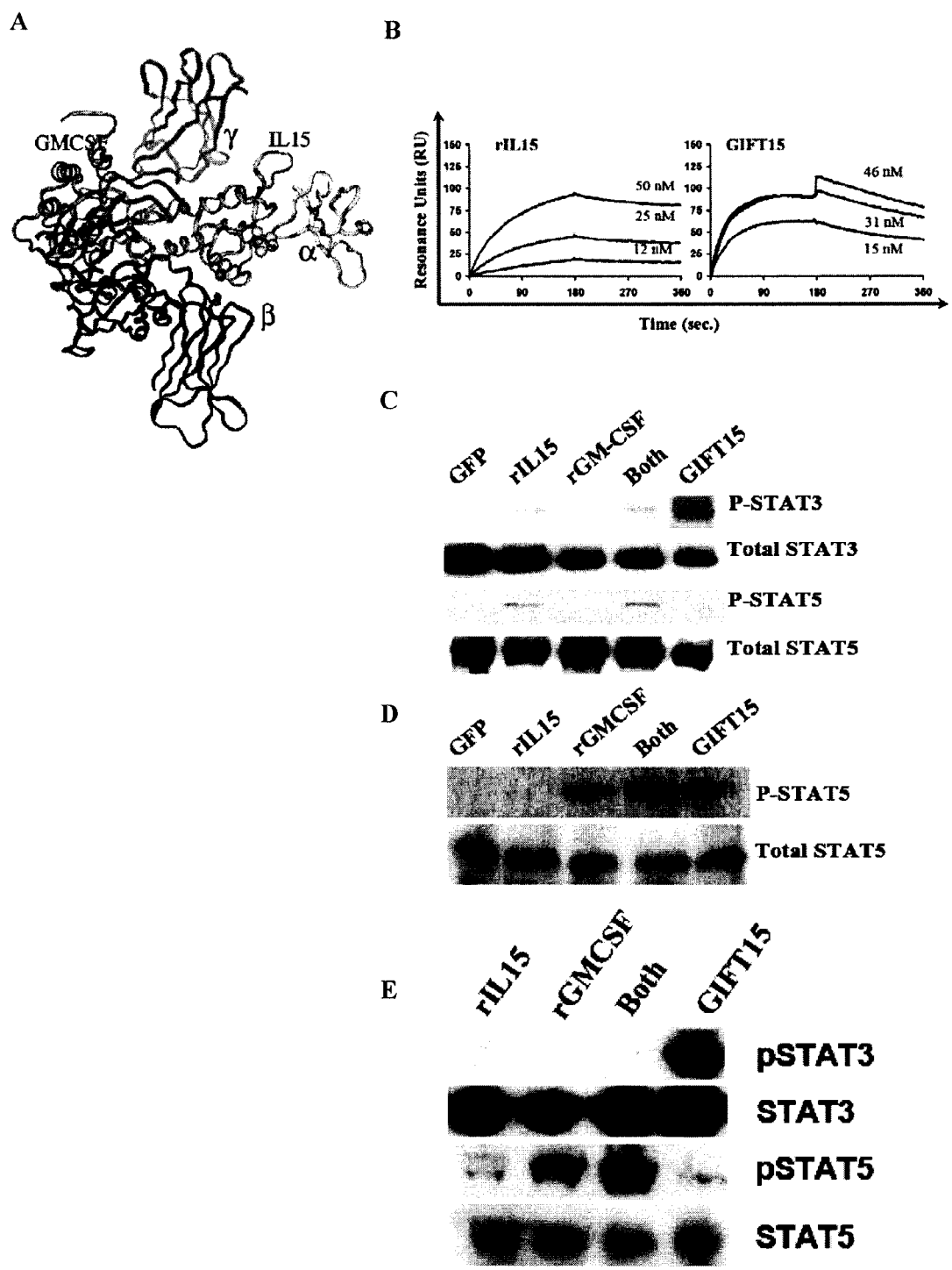

FIG. 11 Signalling of mouse and human GIFT15 via the GM-CSF receptor (GM-CSFR) and IL-15R. (a) Structural model of mGIFT15 (green, grey and cyan ribbon) complexed with IL15Rα (yellow ribbon), IL2Rβ (purple ribbon) and IL2Rγ (red ribbon). (b) Surface Plasmon Resonance (SPR) analysis of the IL-15Rα chain interaction with rIL-15 and purified mGIFT15 as shown in a BIAcore sensorgram. (c) Increased STAT3 phosphorylation induced by mGIFT15 in splenocytes expressing only the IL-15R. (d) Unchanged STAT5 phosphorylation in JAWSII cells expressing only the GM-CSFR. (e) Increased STAT3 and decreased STAT5 phosphorylation induced by mGIFT15 in macrophages expressing both, IL-15R and GM-CSFR.

Figure 12:
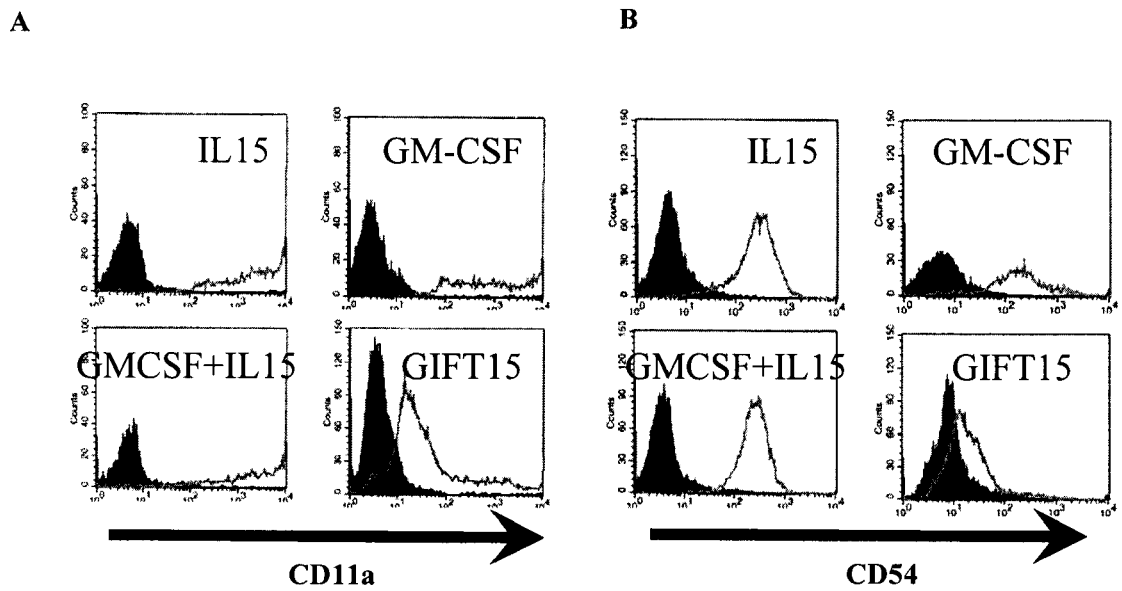

FIG. 12 Downregulation of the adhesion molecules (a) LFA-1/CD11a and (b) ICAM-1/CD54 by mGIFT15 contrary to their upregulation by IL-15, GM-CSF and their combination.

Figure 13:
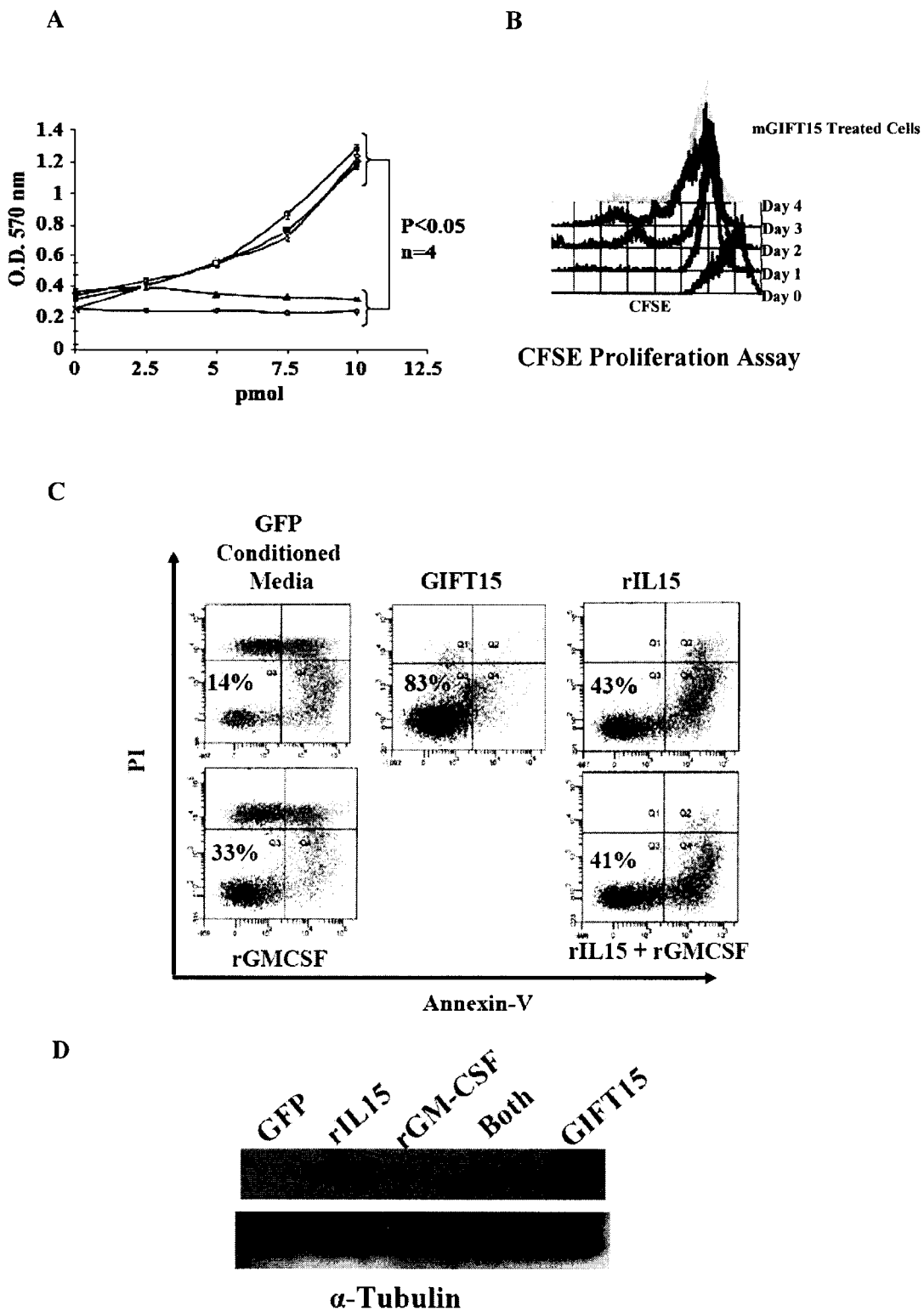

FIG. 13 Anti-apoptotic and proliferative activities of mGIFT15. (a) Proliferation inducing potential of mGIFT15 as demonstrated in a MTT (dye) incorporation assay and a CFSE (dye) based assay as shown in (b). (c) Anti-apoptotic potential of mGIFT15 as demonstrated with a PI and Annexin V flow cytometry read-out and a Bcl-XL Western blot (d).

Figure 14:
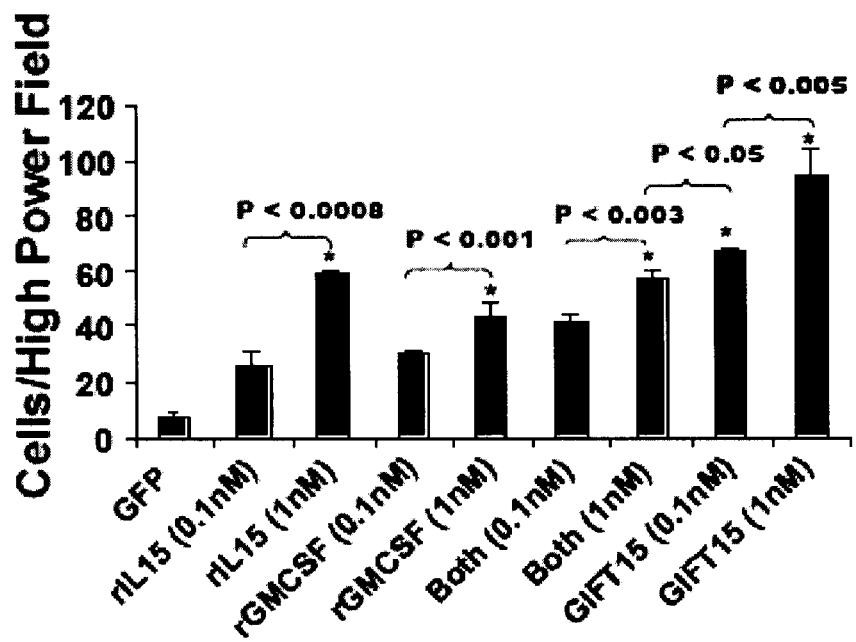
Figure 14:
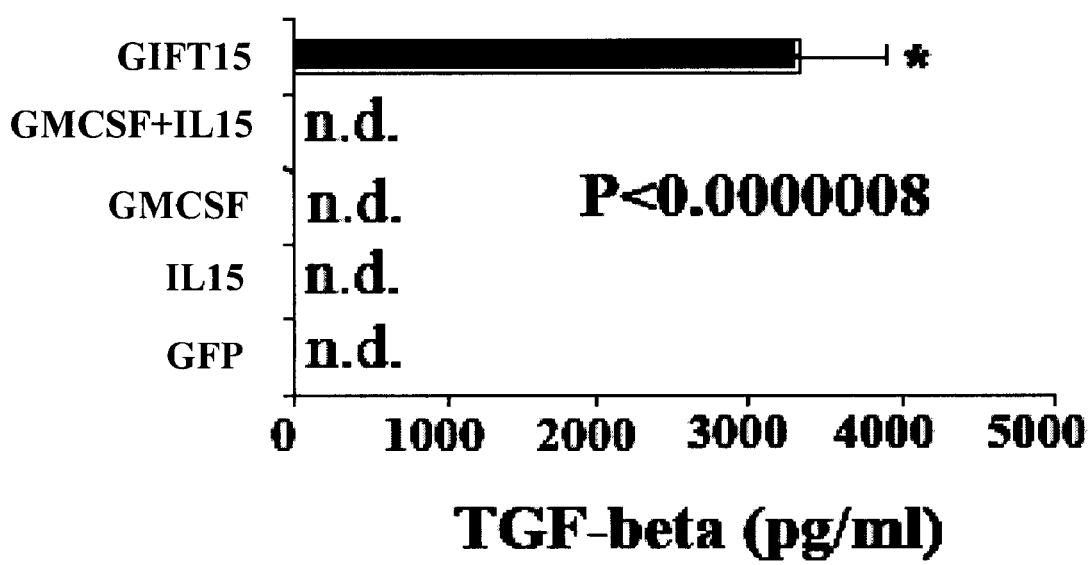

FIG. 14 Increased recruitment of macrophages and secretion of transforming growth factor (TGF)-β induced by mGIFT15. (a) Migration assay with peritoneal macrophages in the presence of cytokines. (b) TGFβ levels secreted by peritoneal macrophages stimulated with mGIFT15 as detected in an ELISA.

Figure 15:
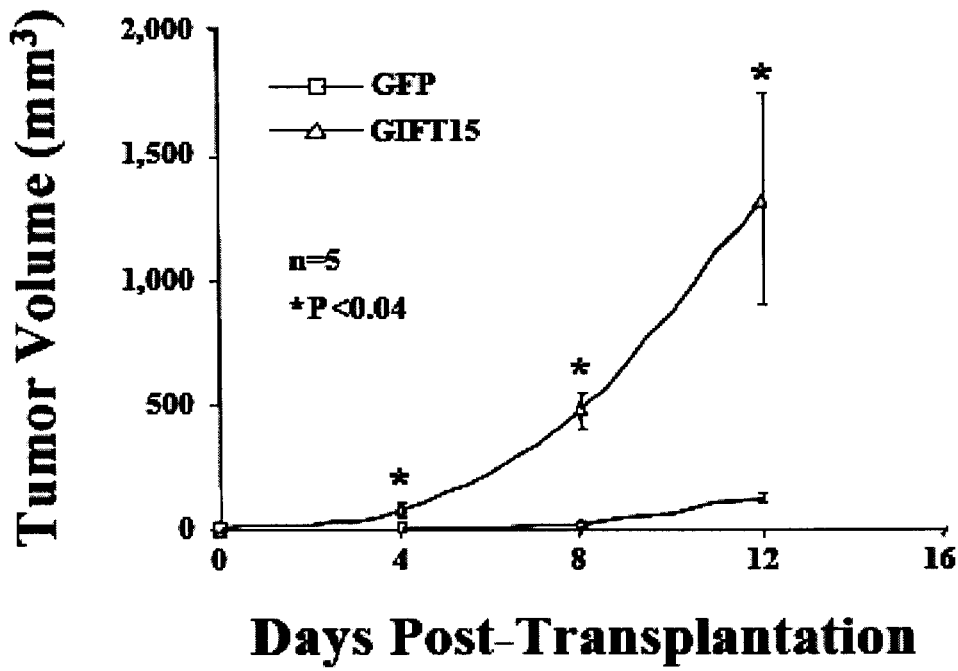
Figure 15:
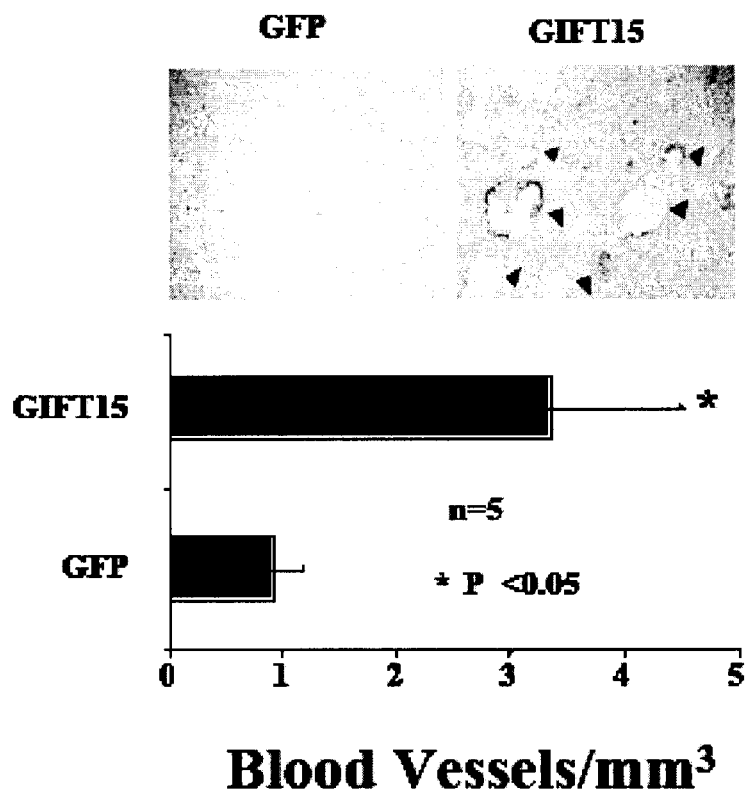

FIG. 15 Pro-angiogenic properties of mGIFT15 in-vivo. (a) Tumor volume assessed in NOD-SCID mice injected with B16F0 cancer cells transduced with mGIFT15. (b) Increased blood vessel density in tumors arising from mGIFT15 transduced cancer cells as confirmed by staining with an anti van Willebrand Factor (vWF) antibody.

Figure 16:
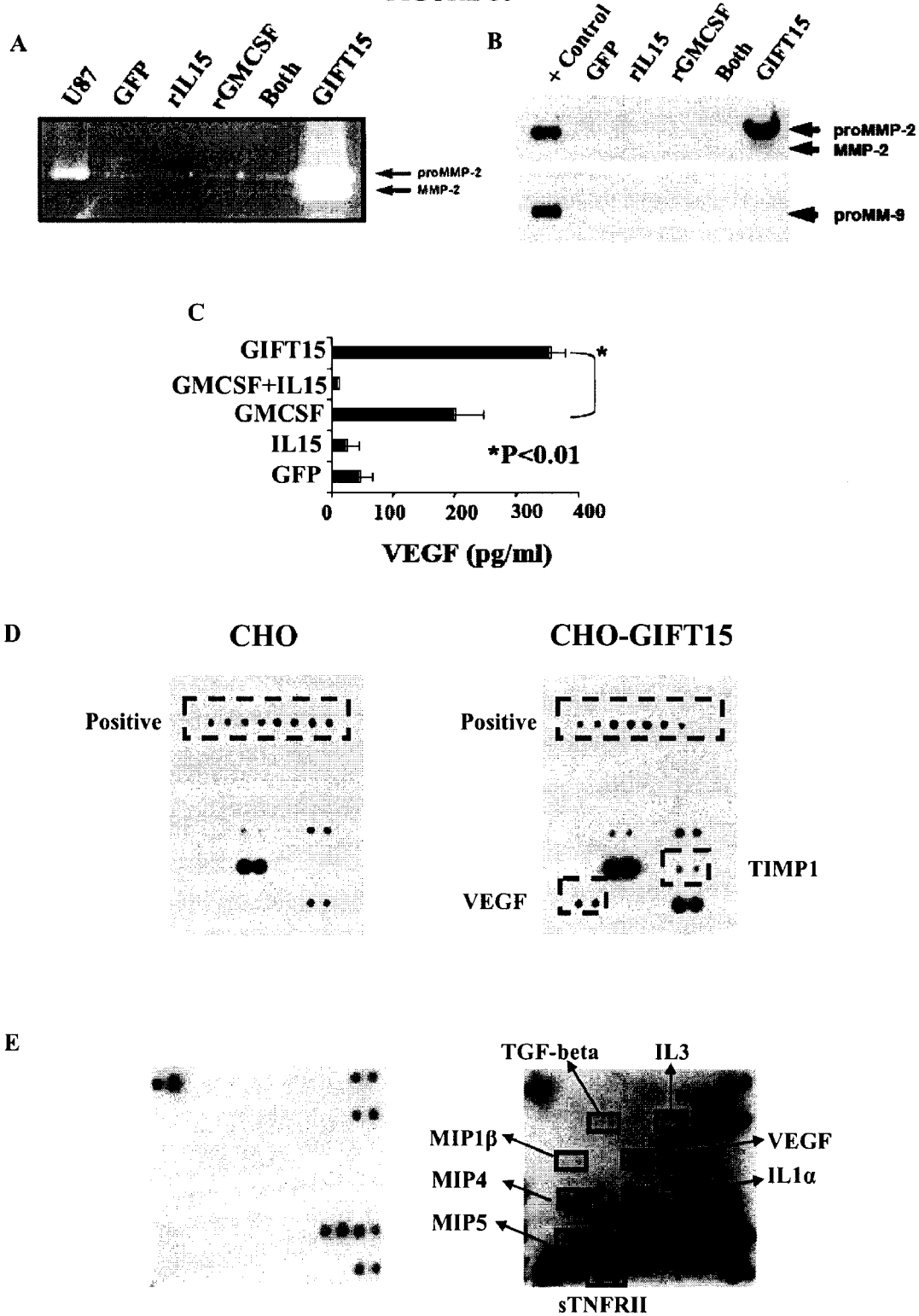

FIG. 16 Pro-angiogenic properties of murine and human GIFT15 in-vitro. (*a*) Secretion and activation of Matrix metalloproteinase (MMP-)2 induced by mGIFT15 in serum deprived macrophages as confirmed in a gelatin zymogram. (*b*) Induction of MMP-2 but not MMP-9 by mGIFT15 as confirmed by Western Blot. (*c*) Increased induction of the pro-angiogenic Vascular Endothelial Growth Factor (VEGF) by mGIFT15 in macrophages. (*d*) Induction of the angiogenic factors Tissue metalloproteinase (TIMP)-1 and VEGF by hGIFT15 derived from Chinese Hamster Ovary (CHO) cells transduced with the fusokine as demonstrated in an angiogenic protein array. (*e*) Confirmation of VEGF secretion induced by hGIFT15 in a generic cytokine array in addition to the anti-inflammatory molecules TGF-beta and soluble Tumor Necrosis Factor Receptor (sTNFR)II.

Figure 17:
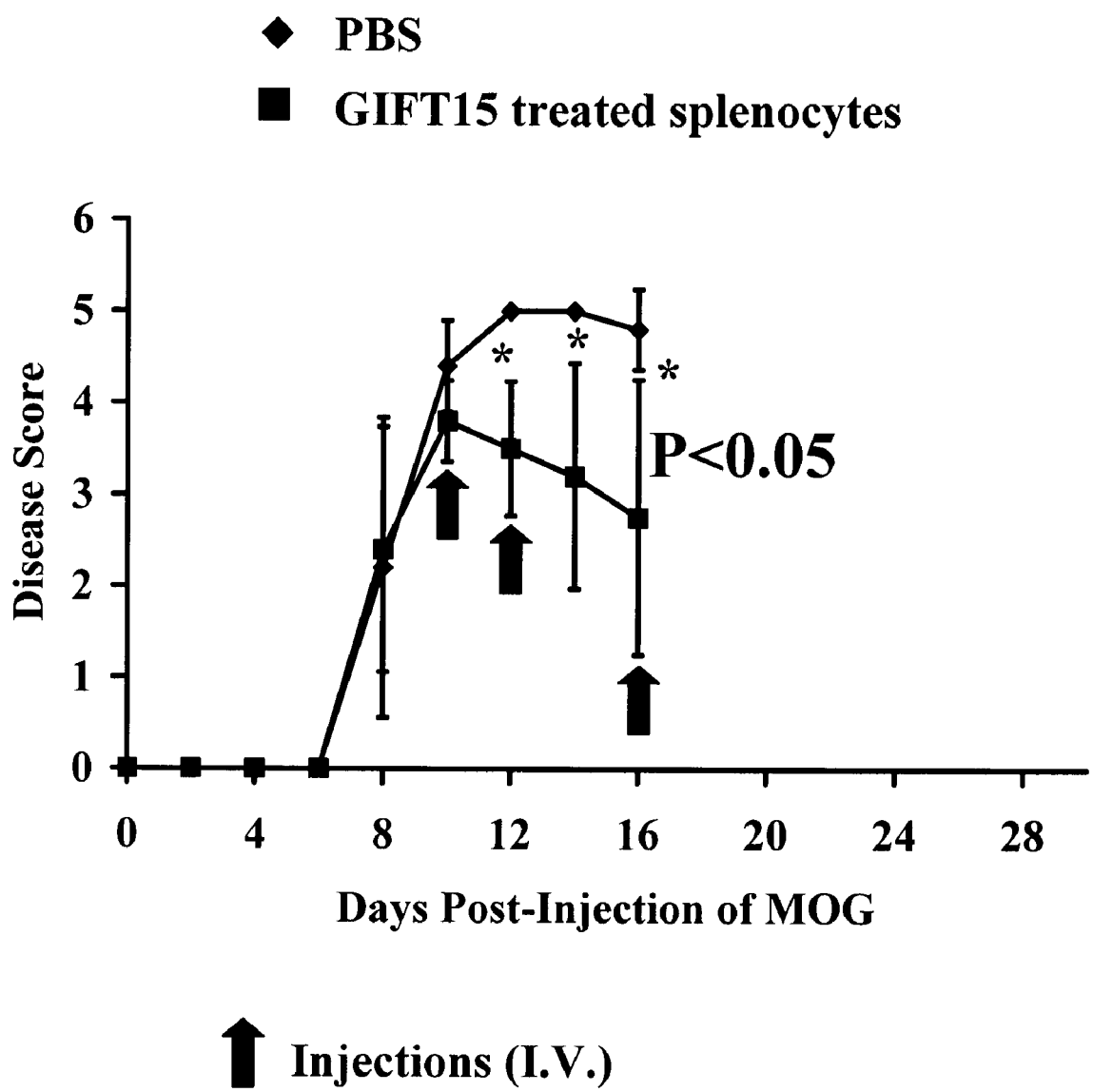

FIG. 17 GIFT15 Treated Splenocytes lead to faster recovery in syngeneic C57BI/6 EAE mice. Mice injected with MOG to induce EAE received 3 IV injections of C57BI/6 GIFT15-treated splenocytes and the disease score was monitored every second day. Compared to the PBS control group, GIFT15 treated splenocytes lead to a faster recovery starting at day 12 (n=5/group; P<0.05).

DETAILED DESCRIPTION OF THE INVENTION

The present inventors have shown that a conjugate comprising GM-CSF and IL-15 has immune suppressive properties. Further, the inventors have shown that the conjugate can be used to prevent graft rejection, including xenograft rejection; prevent or treat graft versus host disease; prevent or treat autoimmune disease; and to inhibit cell death. The inventors have also shown that administering the GM-CSF and IL-15 conjugate induces angiogenesis.

The inventors have demonstrated that the GM-CSF and IL-15 conjugate possesses novel biochemical properties leading to altered affinities to components of the trimeric IL-15R and asymmetrical downstream signalling via its two STAT/JAK pathways in lymphoid cells. As a result, cellular proliferation, reduced apoptosis and blunting of the IFNγ response following activation can be achieved. The sum of these effects mediates a profound immunosuppressive state permissive to xenotransplantation which is CD4 dependent.

A. GM-CSF and IL-15 Conjugates

The present invention relates to conjugates of GM-CSF and IL-15 that are immune suppressive and can be used in various therapeutic applications as described in Section B.

Accordingly, the present invention provides a GM-CSF and IL-15 conjugate protein.

The term "a GM-CSF and IL-15 conjugate protein" means a conjugate that comprises GM-CSF physically linked to IL-15. In a specific embodiment, the conjugate is a fusion protein (or fusokine) wherein a nucleic acid sequence encoding GM-CSF is operably linked to a nucleic acid sequence encoding IL-15 and the chimeric sequence is transfected or transduced into a host cell and produced as a recombinant fusion protein. The GM-CSF and IL-15 fusion protein is often abbreviated GIFT15 in the present application.

In a specific embodiment, the GM-CSF and IL-15 are linked by a peptide linker. The peptide linker can be any size provided it does not interfere with the function of the GM-CSF and IL-15 conjugate. In one embodiment, the peptide linker is from about 2 to about 15 amino acids in length, more specifically from about 2 to about 10 amino acids, and most specifically from about 2 to about 7 amino acids.

One of skill in the art can appreciate that the GM-CSF and IL-15 conjugate protein can also be formed by linking the two proteins in vitro, for example, using chemical cross-linkers. For example, the proteins may be coupled using heterobifunctional thiol-containing linkers as described in WO 90/10457, N-succinimidyl-3-(2-pyridyldithio-proprionate) or N-succinimidyl-5 thioacetate.

The GM-CSF and IL-15 molecules used in the conjugate can be from any species or source and includes the full-length proteins as well as fragments or portions of the proteins. In a preferred embodiment, the GM-CSF and IL-15 sequences are from human or mouse. In a specific embodiment, the GM-CSF protein lacks the last 11 carboxy terminal amino acid sequences as compared to full length GM-CSF.

In one embodiment, the GM-CSF and IL-15 conjugate protein is murine and has the amino acid sequence shown in SEQ ID NO:2 or an analog or homolog thereof. In another embodiment, the GM-CSF and IL-15 conjugate protein is human and has the sequence shown in SEQ ID NO:4 or an analog or homolog thereof.

The invention also includes nucleic acid molecules that encode the GM-CSF and IL-15 protein conjugate. The nucleic acid molecule is preferably a chimeric nucleic acid sequence that comprises a) a nucleic acid sequence encoding GM-CSF or a fragment thereof linked to b) a nucleic acid sequence encoding IL-15 or a fragment thereof.

The chimeric sequence preferably also includes a sequence encoding a peptide linker. Accordingly, the present invention also includes a chimeric nucleic acid sequence that comprises a) a nucleic acid sequence encoding GM-CSF or a fragment thereof linked to b) a nucleic acid sequence encoding a peptide linker linked to c) a nucleic acid sequence encoding IL-15 or a fragment thereof.

In one embodiment, the chimeric nucleic acid sequence is murine and has the sequence shown in SEQ ID NO:1, or a homolog or analog thereof. In another embodiment, the chimeric nucleic acid sequence is human and has the sequence shown in SEQ ID NO:3, or a homolog or analog thereof.

The term "homolog" means those amino acid or nucleic acid sequences which have slight or inconsequential sequence variations from the sequences in SEQ ID NOs:1-4, i.e., the sequences function in substantially the same manner. The variations may be attributable to local mutations or structural modifications. Sequences having substantial homology include nucleic acid sequences having at least 65%, more preferably at least 85%, and most preferably 90-95% identity with the sequences as shown in SEQ ID NOs:1-4. Sequence identity can be calculated according to methods known in the art. Nucleic acid sequence identity is most preferably assessed by the algorithm of BLAST version 2.1 advanced search. BLAST is a series of programs that are available online at http://www.ncbi.nlm.nih.gov/BLAST. The advanced blast search (http://www.ncbi.nlm.nih.gov/blast/blast.cgi?Jform=1) is set to default parameters. (ie Matrix BLOSUM62; Gap existence cost 11; Per residue gap cost 1; Lambda ratio 0.85 default). References to BLAST searches are: Altschul, S. F., Gish, W., Miller, W., Myers, E. W. & Lipman, D. J. (1990) "Basic local alignment search tool." J. Mol. Biol. 215:403-410; Gish, W. & States, D. J. (1993) "Identification of protein coding regions by database similarity search." Nature Genet. 3:266272; Madden, T. L., Tatusov, R. L. & Zhang, J. (1996) "Applications of network BLAST server" Meth. Enzymol. 266:131__141; Altschul, S. F., Madden, T. L., Schäffer, A. A., Zhang, J., Zhang, Z., Miller, W. & Lipman, D. J. (1997) "Gapped BLAST and PSI_BLAST: a new generation of protein database search programs." Nucleic Acids Res. 25:33893402; Zhang, J. & Madden, T. L.

(1997) "PowerBLAST: A new network BLAST application for interactive or automated sequence analysis and annotation." Genome Res. 7:649656.

The term "analog" means an amino acid or nucleic acid sequence which has been modified as compared to the sequence of SEQ ID NOs:1-4 wherein the modification does not alter the utility of the sequence (e.g. as immune suppressant) as described herein. The modified sequence or analog may have improved properties over the sequences shown in SEQ ID NOs:1-4. One example of a nucleic acid modification to prepare an analog is to replace one of the naturally occurring bases (i.e. adenine, guanine, cytosine or thymidine) of the sequence with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecules shown in SEQ ID NO:1 or 3. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

The invention also includes sequences that hybridize to the sequences shown in SEQ ID NO:1 or 3 or a fragment thereof. The term "sequence that hybridizes" means a nucleic acid sequence that can hybridize to a sequence of SEQ ID NO:1 or 3 under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. The term "stringent hybridization conditions" as used herein means that conditions are selected which promote selective hybridization between two complementary nucleic acid molecules in solution. Hybridization may occur to all or a portion of a nucleic acid sequence molecule. The hybridizing portion is at least 50% the length with respect to one of the polynucleotide sequences encoding a polypeptide. In this regard, the stability of a nucleic acid duplex, or hybrids, is determined by the Tm, which in sodium containing buffers is a function of the sodium ion concentration, G/C content of labeled nucleic acid, length of nucleic acid probe (I), and temperature (Tm=81.5° C.−16.6 (Log 10[Na+])+0.41(%(G+C)−600/l). Accordingly, the parameters in the wash conditions that determine hybrid stability are sodium ion concentration and temperature. In order to identify molecules that are similar, but not identical, to a known nucleic acid molecule a 1% mismatch may be assumed to result in about a 1° C. decrease in Tm, for example if nucleic acid molecules are sought that have a greater than 95% identity, the final wash will be reduced by 5° C. Based on these considerations stringent hybridization conditions shall be defined as: hybridization at 5× sodium chloride/sodium citrate (SSC)/5×Denhardt's solution/1.0% SDS at Tm (based on the above equation)−5° C., followed by a wash of 0.2×SSC/0.1% SDS at 60° C.

It will be appreciated that analogs/homologs of the GM-CSF and IL-15 conjugate can also be prepared by first preparing or using an analog or homolog of GM-CSF or IL-15 or both prior to preparing the chimeric nucleic acid sequence.

The GM-CSF and IL-15 conjugate protein may be modified to contain amino acid substitutions, insertions and/or deletions that do not alter the immunosuppressive properties of the protein. Conserved amino acid substitutions involve replacing one or more amino acids of the GM-CSF and IL-15 conjugate protein with amino acids of similar charge, size, and/or hydrophobicity characteristics. When only conserved substitutions are made the resulting analog should be functionally equivalent to the GM-CSF and IL-15 conjugate protein. Non-conserved substitutions involve replacing one or more amino acids of the GM-CSF and IL-15 conjugate protein with one or more amino acids which possess dissimilar charge, size, and/or hydrophobicity characteristics.

The GM-CSF and IL-15 conjugate protein may be modified to make it more therapeutically effective or suitable. For example, the GM-CSF and IL-15 conjugate protein or peptides of the present invention may be converted into pharmaceutical salts by reacting with inorganic acids including hydrochloric acid, sulphuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benzenesulphonic acid, and toluenesulphonic acids.

The invention also includes expression vectors comprising a chimeric nucleic acid sequence comprising a) a nucleic acid sequence encoding GM-CSF or a fragment thereof linked to b) a nucleic acid sequence encoding IL-15 or a fragment thereof. In a specific embodiment, the chimeric nucleic acid sequence includes a sequence that encodes a peptide linker as described above.

Possible expression vectors include but are not limited to cosmids, plasmids, artificial chromosomes, viral vectors or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which is operatively linked to the nucleic acid molecule. Operatively linked is intended to mean that the nucleic acid is linked to regulatory sequences in a manner which allows expression of the nucleic acid.

The invention therefore contemplates a recombinant expression vector of the invention containing a nucleic acid molecule of the invention, or a fragment thereof, and the necessary regulatory sequences for the transcription and translation of the inserted protein-sequence.

Suitable regulatory sequences may be derived from a variety of sources, including bacterial, fungal, viral, mammalian, or insect genes (for example, see the regulatory sequences described in Goeddel, Gene Expression Technology Methods in Enzymology 185, Academic Press, San Diego, Calif. (1990). Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the GM-CSF or IL-15 sequences and/or their flanking regions.

The recombinant expression vectors of the invention may also contain a selectable marker gene which facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, firefly luciferase, or an immunoglobulin or portion thereof such as the Fc portion of an immunoglobulin preferably IgG. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

The recombinant expression vectors may also contain genes which encode a moiety which provides increased expression of the recombinant protein; increased solubility of the recombinant protein; and aid in the purification of the target recombinant protein by acting as a ligand in affinity purification. For example, a proteolytic cleavage site may be added to the target recombinant protein to allow separation of the recombinant protein from the fusion moiety subsequent to purification of the fusion protein. Typical fusion expression vectors include pGEX (Amrad Corp., Melbourne, Australia), pMal (New England Biolabs, Beverly, Mass.) and pRIT5 (Pharmacia, Piscataway, N.J.) which fuse glutathione S-transferase (GST), maltose E binding protein, or protein A, respectively, to the recombinant protein.

Recombinant expression vectors can be introduced into host cells to produce a transformed host cell. The term "transformed host cell" is intended to include cells that are capable of being transformed or transfected with a recombinant expression vector of the invention. The terms "transduced", "transformed with", "transfected with", "transformation" and "transfection" are intended to encompass introduction of nucleic acid (e.g. a vector or naked RNA or DNA) into a cell by one of many possible techniques known in the art. Prokaryotic cells can be transformed with nucleic acid by, for example, electroporation or calcium-chloride mediated transformation. For example, nucleic acid can be introduced into mammalian cells via conventional techniques such as calcium phosphate or calcium chloride co-precipitation, DEAE-dextran mediated transfection, lipofectin, electroporation, microinjection, RNA transfer, DNA transfer, artificial chromosomes, viral vectors and any emerging gene transfer technologies. Suitable methods for transforming and transfecting host cells can be found in Sambrook et al. (Molecular Cloning: A Laboratory Manual, 2nd Edition, Cold Spring Harbor Laboratory press (1989)), and other laboratory textbooks.

Suitable host cells include a wide variety of eukaryotic host cells and prokaryotic cells. For example, the proteins of the invention may be expressed in yeast cells or mammalian cells. Other suitable host cells can be found in Goeddel, Gene Expression Technology: Methods in Enzymology 185, Academic Press, San Diego, Calif. (1991). In addition, the proteins of the invention may be expressed in prokaryotic cells, such as Escherichia coli (Zhang et al., Science 303(5656): 371-3 (2004)).

Mammalian cells suitable for carrying out the present invention include, among others: B16FO cells, 293T cells, Mesenchymal Stromal Cell (MSCs), COS (e.g., ATCC No. CRL 1650 or 1651), BHK (e.g. ATCC No. CRL 6281), CHO (ATCC No. CCL 61), HeLa (e.g., ATCC No. CCL 2), 293 (ATCC No. 1573) and NS-1 cells.

The mammalian cells can also be derived from a human or animal and include stem cells (including hematopoietic stem cells), somatic cells, progenitor cells (including endothelial progenitor cells), fibroblasts, lymphocytes, and MSCs that have been genetically engineered to express the GM-CSF and IL-15 conjugate. Such cells can be used in the therapeutic applications described in Section B. For example, MSCs, fibroblasts, lymphocytes, hematopoietic stem cells derived from human or non-human sources can be gene engineered to express the GM-CSF and IL-15 conjugate and serve for cellular therapy of disease such as heart disease, neurodegeneration, diabetes mellitus, muscle dystrophy and hematopoietic disorders.

Suitable expression vectors for directing expression in mammalian cells generally include a promoter (e.g., derived from viral material such as polyoma, Adenovirus 2, cytomegalovirus and Simian Virus 40), as well as other transcriptional and translational control sequences. Examples of mammalian expression vectors include pCDM8 (Seed, B., Nature 329:840 (1987)), pMT2PC (Kaufman et al., EMBO J. 6:187-195 (1987)) and pCMV (Clontech, California, U.S.A.).

Alternatively, the proteins of the invention may also be expressed in non-human transgenic animals such as, rats, rabbits, sheep and pigs (Hammer et al. Nature 315:680-683 (1985); Palmiter et al. Science 222:809-814 (1983); Brinster et al. Proc. Natl. Acad. Sci. USA 82:4438-4442 (1985); Palmiter and Brinster Cell 41:343-345 (1985) and U.S. Pat. No. 4,736,866). The invention also includes tissues and cells derived from such animals.

In a specific embodiment, to create a mouse GM-CSF and IL-15 fusokine, the cDNA of mouse GM-CSF was modified to remove the nucleotides coding for the last 11 carboxyterminal aa and cloned in frame to the 5' end of the full-length mouse IL-15 cDNA, including its long signal peptide[11,12]. Including a synthetic linker bridge consisting of 7 aa between the GM-CSF and IL-15 sequences, the final fusokine mGIFT15 cDNA shown in SEQ ID NO1 encodes for a single polypeptide chain of 299 aa (FIG. 1a) as shown in SEQ ID NO:2. A computer-based analysis of the three-dimensional structure revealed that the 7 aa peptidic bridge and the uncleaved IL-15 long signal peptide sequence forms an intercytokine bridge of 55 aa in length with a three alpha helixes configuration. (FIG. 1b). Denaturing immunoblotting performed on conditioned media (CM) from retrovirally transduced B16F0 cells to express mGIFT15 showed that the chimeric protein is efficiently secreted in the extracellular space and has a molecular weight of 55 kDa. mGIFT15 was probed with polyclonal goat anti-mIL15 or anti-mGMCSF antibodies. While CM containing green fluorescent protein (GFP) served as a negative control, rmIL15 and rmGMCSF were used as positive controls. (FIG. 1c). The bioactivity of both cytokine subunits within GIFT15 was confirmed by proliferation assays based on MTT incorporation in the GM-CSF-dependent JAWSII and IL-15-dependent CTLL2 cell lines, respectively Results are shown as mean of triplicates±S.E.M of one representative experiment of three with a P>0.05 between mGIFT15 and IL15 in CTLL-2 cells and a P>0.05 between mGIFT15 and GMCSF for JAWSII cells. (FIG. 1d).

In another specific embodiment, to create the human GM-CSF and IL-15 fusokine, the cDNA of human GM-CSF was modified to remove the nucleotides coding for the last 11 carboxyterminal aa and cloned in frame to the 5' end of the full-length human IL-15 cDNA, including its long signal peptide[11,12]. Including a synthetic linker peptidic bridge of 2 aa and the uncleaved hIL-15 secretion peptide between the GM-CSF and IL-15 sequences, the final fusokine hGIFT15 cDNA encodes for a single polypeptide chain of 297 aa as shown in SEQ ID NO:4 (FIG. 1e). hGIFT15 expressed in 293T cells was identified as a 55 kDa protein and as multimeric forms as demonstrated in a Western blot involving antibodies directed against human IL-15 and human GM-CSF (FIG. 1f).

B. Therapeutic Methods

The invention includes all applications of the GM-CSF and IL-15 conjugate, some of which are described below.

1. Immune Suppression

To assess the ability of GIFT15 to influence the immune response, polyclonal populations of $10^6$ B16F0 cancer cells genetically engineered to secrete equimolar levels of IL-15, GM-CSF or GIFT15 were subcutaneously injected in syngeneic immune competent C57Bl/6 mice (n=6). Unexpectedly, the fusokine comprising the two immunostimulatory subunits IL-15 and GM-CSF, had the opposite, an immunosuppressive, effect. It was observed that B16F0 cells secreting GIFT15 had acquired aggressive growth properties with an average tumor size three fold larger than that of control groups in the weeks following implantation. Tumor volume was monitored over time resulting in a Pvalue of <0.05 between B16-mGIFT15 and B16-GFP/mIL15/mGMCSF/mIL15+mGMCSF. Results are shown as mean tumor volume±S.E.D. (FIG. 2a). To determine whether this phenomenon was linked to an atypical immune response, the inventors analyzed tumor infiltration by immune cells a fortnight after implantation of Matrigel™ matrix embedded cells. It was found that natural killer (NK) and natural killer T (NKT) cells were virtually absent in GIFT15-secreting tumors when compared to B16-GM-CSF or B16-IL-15 control groups whilst the number of other CD3+ T-cell subsets were similar to controls (FIG. 2b). The observed absence in NK/NKT cell recruitment by B16-GIFT15 cells is contradictory to what was predicted would occur as a host-derived immune response to GIFT15 in vivo, especially since IL-15 has been shown by others to directly stimulate the development, expansion, recruitment and activation of NK and NKT cells[13,14].

In one aspect, the present invention provides a method of suppressing an immune response comprising administering an effective amount of a GM-CSF and IL-15 conjugate protein or a nucleic acid sequence encoding a GM-CSF and IL-15 conjugate protein to an animal in need of such treatment. The invention includes a use of an effective amount of a GM-CSF and IL-15 conjugate protein or a nucleic acid sequence encoding a GM-CSF and IL-15 conjugate protein to suppress an immune response. The invention includes a use of an effective amount of a GM-CSF and IL-15 conjugate protein or a nucleic acid sequence encoding a GM-CSF and IL-15 conjugate protein to prepare a medicament to suppress an immune response. In a specific embodiment, the conjugate inhibits the development, expansion or activation of NK cells, NKT cells, T cells or B cells.

The term "administering a GM-CSF and IL-15 conjugate protein" includes both the administration of the GM-CSF and IL-15 conjugate protein as well as the administration of a nucleic acid sequence encoding a GM-CSF and IL-15 conjugate protein to an animal or to a cell in vitro or in vivo. The term "administering" also includes the administration of a cell that express the GM-CSF and IL-15 conjugate protein.

The term "a cell" includes a single cell as well as a plurality or population of cells. Administering to a cell includes administering in vitro (or ex vivo) as well as in vivo.

Administration of an "effective amount" of the GM-CSF and IL-15 conjugate protein and nucleic acid of the present invention is defined as an amount effective, at dosages and for periods of time necessary to achieve the desired result. The effective amount of the GM-CSF and IL-15 conjugate protein or nucleic acid of the invention may vary according to factors such as the disease state, age, sex, and weight of the animal. Dosage regimens may be adjusted to provide the optimum therapeutic response. For example, several divided doses may be administered daily or the dose may be proportionally reduced as indicated by the exigencies of the therapeutic situation. The mode of administration (e.g. in vivo by injection or ex vivo in culture) will also impact the dosage regime.

The term "animal" as used herein includes all members of the animal kingdom including humans.

Once a particular GM-CSF and IL-15 conjugate protein or analog or homolog is prepared, one of skill in the art can readily determine whether or not it can suppress an immune response. For example, determining whether a particular GM-CSF and IL-15 conjugate protein or fragments thereof can suppress an immune response can be assessed using known in vitro immune assays including, but not limited to, inhibiting a mixed leucocyte reaction; inhibiting a cytotoxic T cell response; inhibiting interleukin-2 production; inhibiting IFN-γ production; inhibiting a Th1 cytokine profile; inducing IL-4 production; inducing TGFβ production; inducing IL-10 production; inducing a Th2 cytokine profile; inhibiting immunoglobulin production; altering serum immunoglobulin isotype profiles (from those associated with Th1 type immunity—in the mouse, IgG1 and IgG2a, to those associated with Th2 type immunity—in the mouse, IgG2b, IgG3); and any other assay that would be known to one of skill in the art to be useful in detecting immune suppression.

(i) Graft Rejection

In light of the unheralded immunosuppressive effects of GIFT15, the inventors tested whether its expression could protect allogeneic cells from rejection in immune competent MHC-mismatched recipient animals. As proof of concept, $10^7$ B16-GFP or B16-GIFT15 ($H-2K^b$) transduced cells were grafted in BALB/c ($H-2K^d$) mice (n=10). Surprisingly, tumors secreting the fusion protein were accepted in all mice and grew to a point where half the group had large tumors with volumes exceeding 1,000 mm$^3$ by day 28 post-transplantation (P<0.05 between B16-mGIFT15 and GFP group). Results are shown as mean tumor volume±S.E.D. (FIG. 3a). In addition, these mice developed splenomegaly (FIG. 3b;

P<0.02) characterized by the disappearance of the spleen's white pulp structures demonstrated by H & E staining and by a significant increase in the absolute number in T and NK cells demonstrated by flow cytometry analysis. (n=3; P<0.02 between the mGIFT15 and GFP group). Results are shown as mean average of triplicates±S.E.D. (FIG. 3c) contrary to the unexpected decrease or absence of NK cells in the tumor tissue as described in FIG. 2b. The inventors further investigated the utility of GIFT15 for the induction of immunosuppression in the context of xenotransplantation. In this case, a mGIFT15 transduced polyclonal population of the human glioma cell line U87GM secreting 1119 ng per $10^6$ cells per 24 hrs of GIFT15 was transplanted subcutaneously in BALB/c mice (n=6). All mice accepted the GIFT15 xenograft for up to 8 months whereas the control U87-GFP xenograft was rejected 12 days post-injection (FIG. 3d). As different mouse strains generate variable immune responses, the inventors pursued the studies by xenotransplanting C57BI/6 mice, which are known to possess a biased T-helper 1 immune response[15,16]. Even though both GFP and GIFT15 xenografts were rejected in these mice, there was a two-month delay for the complete regression of the U87-GIFT15 transplants compared to the U87-GFP group (FIG. 3e). Experiments performed in KO mice revealed that CD8 T-cell activity does not seem to be implicated since a similar rejection profile of U87-GIFT15 was obtained in $CD8^{-/-}$ mice compared to wild-type (WT) C57BI/6 mice (FIG. 3e). However, NK cells were found to be key players for the xenograft rejection in WT C57BI/6 since 80% of mice having an NK deficiency (beige mice) accepted the transplants for a period longer than 120 days (FIG. 3e). In addition, the immunosuppressive property of the fusion protein was impaired once U87-GIFT15 transduced cells were injected in $CD4^{-/-}$ model of C57BI/6 mice (FIG. 3e). This suggests that the lack of regulatory T-cells (Treg) cells mitigates the effect of GIFT15. Notably, one crucial effect of Tregs is to inhibit NK cell function[17].

In one embodiment, the present invention provides a method of suppressing an immune response to a transplanted organ, cell or tissue in a recipient animal comprising administering an effective amount of a GM-CSF and IL-15 conjugate protein or a nucleic acid sequence encoding a GM-CSF and IL-15 conjugate protein to the recipient animal, preferably prior to the transplantation of the organ or tissue. The invention includes a use of an effective amount of a GM-CSF and IL-15 conjugate protein or a nucleic acid sequence encoding a GM-CSF and IL-15 conjugate protein to suppress an immune response to a transplanted organ, cell or tissue. The invention includes a use of an effective amount of a GM-CSF and IL-15 conjugate protein or a nucleic acid sequence encoding a GM-CSF and IL-15 conjugate protein to prepare a medicament to suppress an immune response to a transplanted organ, cell or tissue.

The recipient can be any member of the animal kingdom including rodents, pigs, cats, dogs, ruminants, non-human primates and preferably humans. The organ, cell or tissue to be transplanted can be from the same species as the recipient (allograft) or can be from another species (xenograft). The tissues, cells or organs can be any tissue or organ including heart, liver, kidney, lung, pancreas, pancreatic islets, brain tissue, cornea, bone, intestine, skin and haematopoietic cells and stem cells.

In one embodiment, the organ, cells or tissue to be transplanted may be transduced with a nucleic acid construct encoding the GM-CSF and IL-15 conjugate prior to transplantation into the graft recipient.

One of skill in the art can determine whether or not a particular GM-CSF and IL-15 conjugate protein or fragment thereof is useful in preventing graft rejection. As mentioned above, one of skill in the art can readily test a GM-CSF and IL-15 conjugate protein or GM-CSF and IL-15 conjugate protein fragment for its ability to suppress an immune response using known in vitro assays. In addition the GM-CSF and IL-15 conjugate protein or GM-CSF and IL-15 conjugate protein fragment can also be tested for its ability to prevent graft rejection in an animal model. For example, one could use the xenotransplant animal model described above.

The method of the invention may be used to prevent graft versus host disease wherein the immune cells in the transplant mount an immune attack on the recipient's immune system. This can occur when the tissue to be transplanted contains immune cells such as when bone marrow or lymphoid tissue is transplanted when treating leukemias, aplastic anemias and enzyme or immune deficiencies, for example.

Accordingly, in another embodiment, the present invention provides a method of preventing or inhibiting graft versus host disease in a recipient animal receiving an organ or tissue transplant comprising administering an effective amount of a GM-CSF and IL-15 conjugate protein or a nucleic acid sequence encoding a GM-CSF and IL-15 conjugate protein to the organ or tissue prior to the transplantation in the recipient animal. The invention includes a use of an effective amount of a GM-CSF and IL-15 conjugate protein or a nucleic acid molecule encoding a GM-CSF and IL-15 conjugate protein to prevent or inhibit graft versus host disease. The invention includes a use of an effective amount of a GM-CSF and IL-15 conjugate protein or a nucleic acid sequence encoding a GM-CSF and IL-15 conjugate protein to prepare a medicament to prevent or inhibit graft versus host disease.

In order to phenotypically characterize the cells involved in the GIFT15 induced immunosuppression the inventors performed two different comparative studies in splenocytes in the presence of IL-5, GM-CSF, both cytokines combined and GIFT15. Since IL-15 is known to be a strong inducer of IFN-γ, the inventors tested the stimulatory capacity of the fusion protein. Splenocytes from C57BL/6 mice stimulated for 36 hrs with 30 pmols of rIL-15 in the absence or presence of rGM-CSF led to similar IFN-γ secretion profiles of suggesting that GM-CSF has no effect on IL-15-mediated IFN-γ production. In contrast, GIFT15 suppressed any IFN-γ secretion in splenocytes at equimolar concentrations to rIL-15 (FIG. 4a; P<0.0005). These unanticipated direct effects of GIFT15 on splenocytes lead to further investigations by flow cytometry. Based on the gates used to analyze splenocytes cultured in the 4 different conditions (IL-15, GM-CSF, both, and GIFT15), the inventors observed a uniform cell population appearing upon GIFT15 treatment compared to the different cytokine conditions (FIG. 4b). Splenocytes treated with mGIFT15 express both MHCI-MHCII at a higher percentage (72%) than the remaining groups (25% for rmIL15, 44% for rmGMCSF or 7% for both) (FIG. 4c). An eight-day treatment with mGIFT15 leads to the expression of MHCII and CD2 in 71% of cells compared to 46-48% MHCII/CD2 double positive cells when treated with single or combined cytokines. (FIG. 4d). To exclude that the CD2 positive cells were B cells, cells were stained for the CD19 B cell marker (FIG. 4e) The cytokine treated splenocytes were also analysed for the presence of CD4, CD8 and NKT cell markers and the dramatic reduction of $CD3^+$ T-cells was only detected in the mGIFT15 subset demonstrating that lymphocytes are not induced to proliferate. (FIG. 4f). Cells were also negative for additional markers, such as CD11b, Gr1, CTLA4, FasL, B7H1, CD80 and CD86 (FIG. 4f).

Since GIFT15 treatment affects T cells as shown with the previous flow cytometry analysis, the inventors sought to determine whether GIFT15 could antagonize IFN-γ secretion arising from a 2-way MLR. Equal numbers of splenocytes (1.5×10$^5$) from BALB/c and C57BI/6 mice were cultured for 72 hrs with or without 180 nM of mGIFT15. Supernatants were tested for IFN-γ by ELISA. The inventors observed a 6 fold decrease in the secretion of this pro-inflammatory cytokine (FIG. 5a). This phenomenon also occurred using the human homolog of GIFT15 on human peripheral blood mononuclear cells (PBMCs) as shown by MLR (FIG. 5b). To investigate the potential indirect inhibitory effect of mGIFT15 on cells in a 2-way MLR, C57BI/6 splenocytes were pre-treated with mGIFT15, GM-CSF or IL-15 for 8 days and subsequently added to BALB/c splenocytes in a 1:1 ratio. Supernatants were tested for IFN-γ after 72 hrs by ELISA. mGIFT15 successfully prevented the production of IFN-γ (FIG. 5c).

Since mGIFT15 treated splenocytes expressed high levels of MHCI and II, the inventors wished to determine their antigen presentation capability. A C57BI/6 hybridoma cell line recognizing OVA peptide in the context of MHCII was added to GIFT15-treated C57BI/6 splenocytes in a 1:1 ratio in an antigen presentation assay. All splenocytes treated with rIL-15, rGM-CSF, both cytokines, and GIFT15 were able to present the peptide in a similar way as shown by the IFN-γ level determined by ELISA. C57BI/6 derived macrophages (Macs) were used as control (FIG. 6a). However, when primary T-cells derived from OTII mice transgenic for a TCR specific for OVA peptide 323-339 presented on MHCII were used, the GIFT15 treated splenocytes prevented T cell activation in contrast to all other cytokine-treated groups (FIG. 6b).

Based on the activation blockade in OTII T cells in the antigen presentation assay, the ability of GIFT15 treated C57BI/6 splenocytes to inhibit antigen presentation in vitro as a bystander cell was assessed. After a 24-hour plating period C57BI/6 peritoneal macrophages were cultured in the presence of rOVA for additional 24 hrs. After washing, T-cells derived from OT-II mice and mGIFT15 treated C57BI/6 splenocytes in a 1:1 ratio were added to the antigen loaded macrophages. Supernatants were tested for IFN-γ production 72 hrs later as a read-out for antigen presentation and T cell activation. mGIFT15 treated C57BI/6 splenocytes prevented the stimulation of primary OTII T cells recognizing OVA antigen presented by C57BI/6 macrophages. Every setup was performed in quadruplets±S.E.D. Interestingly, GIFT15 treated C57BI/6 splenocytes were able to completely block OVA dependent OTII T cell activation as shown by the level of IFN-γ (FIG. 7a). Since IFN-γ can be secreted by either macrophages or T cells, the cellular target inhibited by GIFT15 treated C57BI/6 splenocytes still had to be identified. Peritoneal macrophages were fixed after OVA priming, and subsequently subjected to the same assay. mGIFT15 inhibited IFN-γ production demonstrating that the GIFT15 treated cells were directly inhibiting the OTII T-cells possibly on the level of the immune synapse[18] (FIG. 7b).

Considering that GIFT15 treated C57BI/6 splenocytes inhibited antigen presentation in a syngeneic model and previous MLR data (FIG. 5c), the inventors speculated that GIFT15 treatment of splenocytes could also block an allogeneic stimulation. Using an in vitro model for Graft versus Host Disease structured similar to the antigen presentation assay (FIG. 10a) and IFNγ production as read-out system, the inventors co-cultured C57BI/6 peritoneal macrophages as allogeneic stimulators in ratios varying from 1:1 to 1:5 with BALB/c derived naïve splenocytes in the presence of mGIFT15. It takes up to 4 naïve cells to revert the inhibitory effect of the GIFT15 treated cells (FIG. 10a). As previously shown, the CM of GIFT15 treated splenocytes partially inhibited antigen presentation due to IL10 induction. In a similar effect, GIFT15 derived CM added to the allogeneic reaction led to a strong inhibition of IFNγ (FIG. 10b).

(ii) Autoimmune Disease

Due to the immune suppressive properties of the GM-CSF and IL-15 conjugate, the method of the present invention may be used to treat or prevent autoimmune disease. In an autoimmune disease, the immune system of the host fails to recognize a particular antigen as "self" and an immune reaction is mounted against the host's tissues expressing the antigen. Normally, the immune system is tolerant to its own host's tissues and autoimmunity can be thought of as a breakdown in the immune tolerance system.

Accordingly, in a further embodiment, the present invention provides a method of preventing or treating an autoimmune disease comprising administering an effective amount of a GM-CSF and IL-15 conjugate protein or fragment thereof, or a nucleic acid sequence encoding a GM-CSF and IL-15 conjugate protein or fragment thereof to an animal having, suspected of having, or susceptible to having an autoimmune disease. The invention includes a use of an effective amount of a GM-CSF and IL-15 conjugate protein on a nucleic acid molecule encoding a GM-CSF and IL-15 conjugate protein to prevent or inhibit an autoimmune disease. The invention includes a use of an effective amount of a GM-CSF and IL-15 conjugate protein on a nucleic acid molecule encoding a GM-CSF and IL-15 conjugate protein to prepare a medicament to prevent or inhibit an autoimmune disease.

The term "treatment or treating" as used herein means an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treating" can also mean prolonging survival as compared to expected survival if not receiving treatment.

Autoimmune diseases that may be treated or prevented according to the present invention include, but are not limited to, arthritis, type 1 insulin-dependent diabetes mellitus, adult respiratory distress syndrome, inflammatory bowel disease, dermatitis, meningitis, thrombotic thrombocytopenic purpura, Sjögren's syndrome, encephalitis, uveitis, leukocyte adhesion deficiency, rheumatoid arthritis, rheumatic fever, Reiter's syndrome, psoriatic arthritis, progressive systemic sclerosis, primary biliary cirrhosis, pemphigus, pemphigoid, necrotizing vasculitis, myasthenia gravis, multiple sclerosis, lupus erythematosus, polymyositis, sarcoidosis, granulomatosis, vasculitis, pernicious anemia, CNS inflammatory disorder, antigen-antibody complex mediated diseases, autoimmune haemolytic anemia, Hashimoto's thyroiditis, Graves disease, habitual spontaneous abortions, Reynard's syndrome, glomerulonephritis, dermatomyositis, chronic active hepatitis, celiac disease, tissue specific autoimmunity, degenerative autoimmunity delayed hypersensitivities, autoimmune complications of AIDS, atrophic gastritis, ankylosing spondylitis and Addison's disease.

One of skill in the art can determine whether or not a particular GM-CSF and IL-15 conjugate protein or fragment thereof is useful in preventing autoimmune disease. As mentioned previously, one of skill in the art can readily test a GM-CSF and IL-15 conjugate protein or GM-CSF and IL-15 conjugate protein fragment for its ability to suppress an immune response using known in vitro assays. In addition the GM-CSF and IL-15 conjugate protein or GM-CSF and IL-15 conjugate protein fragment can also be tested for its ability to prevent autoimmune in an animal model. For example, one could use the experimental allergic encephalomyelitis (EAE) model described below wherein the ability of GM-CSF and IL-15 conjugate protein to inhibit IFN-γ secretion is assessed. The EAE model is an animal model for multiple sclerosis. Further, many other autoimmune animal models are available, including, but not limited to, animal models of inflammatory bowel disease (induced by immunization, or developing in cytokine-knockout mice), and models of autoimmune myocarditis and inflammatory eye disease.

As a proof of concept experiment for a disease model, EAE was induced in C57BI/6 mice and splenocytes were then isolated to perform the antigen presentation assay using the MOG peptide as antigen. As shown in FIG. 7c, GIFT15 treated C57BI/6 splenocytes were indeed capable of robustly inhibiting IFN-γ secretion compared to control conditions (rIL-15, rGM-CSF, or both cytokines together). All experiments were performed in quadruplets±S.E.D (P<0.004 between GT-C57BI/6 and the positive control (Macs presenting MOG+EAE T-cells).

After demonstrating in vitro that GIFT15 treated splenocytes were capable of preventing a T cell activation dependent IFN-γ secretion, the inventors tested them in vivo. EAE was induced in C57BI/6 mice. Eight days after injection of MOG$_{35-55}$ animals reached a disease score of 2. Scores 0 to 5 represent the following: scores 0=healthy, 1=floppy tail, 2=difficulties to walk, 3=partial hind limb paralysis, 4=bilateral hind limb paralysis, difficulties to turn over, 5=1-4 and signs of morbidity. They were either left untreated (injected with PBS) as control or injected with 6×10$^6$ GIFT15 treated syngeneic splenocytes on days 9, 12 and 16. The second injection of GIFT15 treated syngeneic splenocytes, led to a significant difference between the treated and the untreated group. Whereas the treated group reached disease score 4 on day 10 and regressed to one of 3 on day 16, the untreated group progressed to disease stage 5 on day 12 continuing until day 16 (FIG. 17)

In order to identify any soluble factor leading to the complete or partial inhibition of T cell activation, C57BI/6 splenocytes were treated with each cytokine for about 4 days then washed and incubated for another 4 days. Following that period, the CM from all groups was collected and added to C57BI/6 macrophages presenting rOVA peptides to OVA specific OTII-derived primary T-cells as previously described (6a). GIFT15 CM again lead to a significant decrease in IFNγ secretion (FIG. 8a). Concurrent experiments demonstrated that GIFT15 leads to a hyperactivation of STAT3 (FIG. 11). As IL-10 is one of the target genes of STAT3, the inventors tested all collected CM for IL10 by ELISA and indeed this suppressive cytokine was induced in cytokine treated C57BI/6 splenocytes, only slightly with both rIL15 and GMCSF but to a higher extent after GIFT15 treatment (FIG. 8b). To prove that IL10 was the only suppressive molecule responsible for the inhibition of T cell activation, the inventors neutralized it with an IL-10 specific antibody. As shown in FIG. 8c, neutralizing IL10 rescues the antigen presentation process to a comparable level with the control condition suggesting that IL10 in the only soluble factor induced following GIFT15 treatment that plays a role in suppressing or inhibiting antigen presentation.

Due to the remarkable inhibitory property of GIFT15 treated C57BI/6 splenocytes on present cell activation, an in vivo experiment was performed to demonstrate the potency of this inhibition directly on humoral responses in mice. Briefly, naïve C57BI/6 mice were immunized with rOVA and once IgM and IgG titers were detectable, GIFT15 treated splenocytes were injected intraperitoneally (IP) and the humoral response (IgM and IgG) monitored weekly. Even though no major changes occurred on the IgM response (FIG. 9A), the IgG end-titer was significantly lower in mice that received the GIFT15 cell therapy as opposed to the control group immunized with rOVA and receiving PBS only (FIG. 9B).

In order to further characterize the molecular mechanism by which GIFT15 exerts its paradoxical suppressive effects on lymphoid cells, the inventors first assessed the interaction of GIFT15 with individual components of the trimeric IL-15R[6,7]. The inventors utilized molecular modelling to predict GIFT15 and IL-15R interaction on a structural level. Based on the known molecular structure of IL-15 interaction with the IL-15Rα chain[19,20] and on the predicted homologous interaction of IL-15 with the IL-15Rβ and γ chains to that of IL2[21], the inventors modeled the best fit for GIFT15 with the trimeric IL-15R (FIG. 11a). This virtual interaction suggests that the GM-CSF domain component of the GIFT15 fusokine may hinder the interaction of the IL-15 domain component with the IL-15Rγ chain, explaining in part the observed down regulation of signalling through the JAK3/STAT5 pathway described in the following. Though the β and γ chains of the IL-15R are components shared by the IL2R complex, the high affinity IL-15Rα chain provides specificity and its binding affinity to GIFT15 was assessed by BIAcore analysis. The inventors found that the average dissociation equilibrium (KD) of rIL-15 was of 3 nM whereas purified GIFT15 interacted with a higher affinity with an average KD of 1.4 nM (FIG. 11b). Since IL-15R-dependent intracellular signalling in immune competent cells occurs through JAK/STAT downstream of both the β chain (JAK1/STAT3) and the γ chain (JAK3/STAT5), the inventors investigated the effect of GIFT15 on these pathways in primary mouse splenocytes expressing only the IL-15R. After 15 minute stimulation with GIFT15 or controls in equimolar concentrations, the inventors found that the fusion protein substantially increased the β chain-dependent phosphorylation of STAT3 and suppressed the γ chain-dependent phosphorylation of STAT5 (FIG. 11c). To determine the effect of GIFT15 on GM-CSFR mediated signalling, the inventors examined STAT5 phosphorylation following stimulation of JAWS-II cells, a GM-CSF-dependent cell line devoid of the IL-15R. The inventors did not observe any difference between GM-CSF and GIFT15 mediated activation of STAT5 in this cell line suggesting that GIFT15 binds and activates the GM-CSFR in a manner indistinguishable to that of GM-CSF by itself (FIG. 11d). This observation suggests that the function of the GM-CSF moiety of GIFT15 remains unchanged despite the tethering of IL-15 at its carboxyterminus. Though the qualitative interaction of GIFT15 with the GM-CSFR appears identical to that of GM-CSF by itself, it must be noted that GM-CSF's half-life in vivo is more than 240 minutes[22,23], whereas IL-15 has a much shorter plasma half-life of less than 1 minute[24]. Therefore, the inventors cannot exclude the possibility that cis-acting effects of the GM-CSF domain on GIFT15 half-life—relative to IL-15—may explain some of the observed phenomena in vivo, especially in regard to its interaction with the IL-15R. To further investigate the potential effect of the fusokine GIFT15 on cells expressing both the IL-15R and GM-CSFR, the inventors performed immunoblotting against STAT proteins in peritoneal macrophages stimulated with 30 pmols of rIL-15, rGM-CSF, both cytokines or purified GIFT15 and demonstrated that STAT3 phosphorylation increased with the fusokine. Purified GIFT15 was used instead of CM in order to avoid macrophage activation due to uptake and presentation of antigen or debris. To the contrary, phosphorylation of STAT5 was comparable to rIL-15 alone but lower compared to both cytokines together (FIG. 11e).

Since STAT3/STAT5 signaling can affect the expression of adhesion molecules[25] important in cell-cell contact and migration especially during pathological conditions the inventors looked at the expression profile of LFA-1 and ICAM-1 both involved in autoimmune diseases, resulting from treatment of splenocytes with rIL15, rGMCSF, both cytokines or GIFT15. In contrast to all control conditions, showing robust expression of CD11a, GIFT15 treatment strongly decreases LFA-1 expression intensity (FIG. 12a). Similar results were obtained for CD54 (ICAM-1) the ligand for LFA-1 (FIG. 12b).

Interestingly, splenocyte proliferation does not seem to be affected by the relative decrease in STAT5 phosphorylation (FIG. 13a; P<0.05) despite the fact that the latter is associated with mitogenic activities[26,27,28]. The proliferative activity was also confirmed using cell labeling with CFSE, a dye intercalating in DNA and lost upon cell division. As such, a subset of splenocytes cultured with mGIFT15 proliferate before loosing CFSE at day 4, whereas the majority of cell either differentiate or do not respond by division (FIG. 13b). Splenocytes stained for propidium iodine (PI) and annexin-V revealed that 83% of cells treated with GIFT15 survived as compared to 33% with rGM-CSF, 43% using rIL-15 or 41% with both molecules (FIG. 13c). In addition, cell lysate immunoblotting against the anti-apoptotic molecule Bcl-XL (FIG. 13d) provides evidence that GIFT15 rescues splenocytes from cell death through an increase in Bcl-XL level, a process known to occur when STAT3 is dominantly activated[29,30].

GIFT15 also affects macrophages by recruiting them and inducing their secretion of TGF-β. As previous data showed that GM-CSF and IL-15 can induce migration of macrophages both in vitro and in vivo[11,12]. The inventors test and confirmed the chemotactic ability of GIFT15 in a macrophage migration assay. GIFT15 derived from the CM of GIFT15-expressing B16F0 cancer cells induced a significant chemotactic effect at a concentration of 0.1 nM compared to CM from GFP-expressing B16F0 cells supplemented with the tenfold and equimolar concentration of 1 nM for both rIL-15 and rGM-CSF (FIG. 14a). In addition, CMs taken from peritoneal macrophages previously stimulated with 30 μM mGIFT15 were tested for the presence of active TGF-β by ELISA. In contrast to control groups, only mGIFT15 led to secretion and/or activation of TGF-β (FIG. 14b).

2. Inducing Angiogenesis

Since GIFT15 was shown to induce immunosuppression in both in vitro and in vivo systems, the inventors tested for additional pharmacological properties. To this effect, the B16F0 tumor cells were used in immunocompromised NOD-SCID mice. An intriguing observation was the significantly enhanced tumorigenicity of B16-GIFT15 cells implanted in NOD-SCID mice where the inventors would have predicted a similar tumor growth rate to controls, if immunosuppression was solely at play (FIG. 15a). The histological analysis of explanted tumors by immunostaining against the endothelial marker Von Willebrand Factor (vWF) revealed a threefold increase in blood vessel density (P<0.05) in B16-GIFT15 tumors compared to the control (FIG. 15b). This phenomenon can be explained in part by the recent discovery that endothelial cells and their progenitors express the IL-15R through which a mitogenic response[31,32] can be initiated. Thus, while GIFT15 facilitates tumor growth in vivo by promoting angiogenesis in addition to its NK and NKT depleting property, both properties also facilitate the survival of solid organ transplants. The GIFT15 induced immunosuppression avoids the activation of the host immune system and its pro-angiogenic effect supports the revascularization of the graft.

The pro-angiogenic effect of mGIFT15 in vivo could be confirmed for mGIFT15 and hGIFT15 in vitro. CM from peritoneal macrophages cultured for 72 hrs with GM-CSF, IL-15, their combination and mGIFT15 were assayed in an angiogenic protein array. When TIMP-2 was induced by mGIFT15 as confirmed by Western blot as a 21 KDa band (data not shown), the inventors tested for the presence of MMP-2 as it is activated by TIMP-2[33] and is involved in angiogenesis[33,34]. The enzymatic ability of MMP-2 was subsequently confirmed by a gelatine zymogram (FIG. 16a) and its identity was differentiated against MMP-9 in a Western blot (FIG. 16b). In addition to MMP-2, VEGF was elevated in the CM collected from GIFT15-treated macrophages compared to those cultured in rmIL-15 in the presence or absence of GM-CSF with lower VEGF levels and GM-CSF alone producing no VEGF similar to the GFP CM control (FIG. 16c). In order to link the mouse data to human in vitro data, human monocytes were tested for their ability to secrete angiogenic factors following hGIFT15 treatment. Angiogenic arrays identified hVEGF and hTIMP-1 (FIG. 16d). hVEGF was also confirmed in a cytokine array, in addition to the anti-inflammatory molecules TGF-β and sTNFRII (FIG. 16e).

Accordingly, in another aspect the present invention provides a method of inducing angiogenesis comprising administering an effective amount of a GM-CSF and IL-15 conjugate protein or a nucleic acid sequence encoding a GM-CSF and IL-15 protein to an animal in need thereof. The invention also includes a use of a GM-CSF and IL-15 conjugate protein or a nucleic acid sequence encoding a GM-CSF and IL-15 protein to induce angiogenesis. The invention also includes a use of a GM-CSF and IL-15 conjugate protein or a nucleic acid sequence encoding a GM-CSF and IL-15 protein to prepare a medicament to induce angiogenesis. In a specific embodiment, the method can be used to support or induce the revascularization of a graft.

Inducing or promoting angiogenesis is useful in treating a number of conditions including, wound healing and conditions where tissue injury induced by ischemia is aggravated by a subsequent inflammatory response. In particular acute myocardial infarction, ischemic stroke, acute renal injury, acute lung injury are examples of conditions where the GM-CSF and IL-15 conjugate could both promote reparative angiogenesis and suppress damaging post-infarction inflammation.

3. Inhibiting Cell Death

In another embodiment of the present invention, the GM-CSF and IL-15 conjugate protein can be used to inhibit the death of a cell. Accordingly, the present invention provides a method of preventing or inhibiting cell death comprising administering an effective amount of a GM-CSF and IL-15 conjugate protein or a nucleic acid sequence encoding a GM-CSF and IL-15 conjugate protein to an animal or cell in need thereof. The invention includes the use of an effective amount of a GM-CSF and IL-15 conjugate protein or a nucleic acid molecule encoding GM-CSF and IL-15 conjugate protein to prevent or inhibit cell death. The invention also includes a use of an effective amount of a GM-CSF and IL-15 conjugate protein or a nucleic acid sequence encoding a GM-CSF and IL-15 conjugate protein to prepare a medicament to prevent or inhibit cell death.

The cell may be any cell for which it is desired to inhibit programmed cell death. Non-limiting examples include a neuronal cell, a cardiac cell or a liver or a hepatic cell. The GM-CSF and IL-15 protein conjugate may be administered in vivo or ex vivo to a cell which is then administered. GM-CSF and IL-15 conjugate protein may be provided alone or with a pharmaceutically acceptable carrier. The carrier may include a diluent. The carrier may include an appropriate adjuvant, a herpes virus, a liposome, a microencapsule, a neuronal cell receptor ligand, a neuronal-specific virus, a polymer encapsulated cell or a retroviral vector. The pharmaceutically acceptable carrier may include an aerosol, intravenous, oral or topical carrier.

Another embodiment of the present invention is a method for treating or alleviating symptoms of a neurodegenerative disorder in a subject which comprises administering to the subject an effective amount of a GM-CSF and IL-15 conjugate protein or a nucleic acid sequence encoding a GM-CSF and IL-15 conjugate protein.

The neurodegenerative disorder may be associated for example with aging, Alzheimer's disease, Parkinson's disease, Huntington's disease, Machoado-Joseph disease, multiple sclerosis, muscular dystrophy, senility, spinocerebellar ataxia type I, spinobulbar muscular atrophy, stroke, trauma. The subject may be a mammal. The mammal may be a human. The administration may include aerosol delivery; intralesional, intraperitoneal, intramuscular or intravenous injection; infusion; liposome-mediated delivery; anal, nasal, oral, ocular, otic or topical such as mucosal delivery of the pharmaceutical composition.

The present invention also provides for a method for alleviating symptoms of a cardiovascular disorder in a subject which comprises administering to a subject an effective amount of a GM-CSF and IL-15 conjugate protein or a nucleic acid sequence encoding a GM-CSF and IL-15 conjugate protein.

The present invention also provides for a method of alleviating symptoms of a liver disorder in a subject which comprises administering to the subject an effective amount of a GM-CSF and IL-15 conjugate protein or a nucleic acid sequence encoding a GM-CSF and IL-15 conjugate protein.

It will be appreciated that the conjugates of the invention can generally be used for treating other symptoms that can be alleviated by inhibiting death in the affected organs or tissues.

In all of the above therapeutic applications, the GM-CSF and IL-15 conjugate can be administered as a protein or as a nucleic acid molecule encoding the protein. In one embodiment, as noted above, expression of the GM-CSF and IL-15 protein conjugate occurs as a result of the administration of nucleic acid encoding GM-CSF and IL-15 protein conjugate to an organism. Thus, GM-CSF and IL-15 protein conjugate will be produced endogenously in the organism, rather than administered in a protein form. The therapy may be done at an embryonic stage of the organism, such that the germ cells of the organism contain GM-CSF and IL-15 protein conjugate nucleic acid, resulting in a transgenic organism, or at a later stage of development to specific somatic cells, such that only a particular tissue or portion of a tissue contains GM-CSF and IL-15 protein conjugate nucleic acid. Techniques for nucleic acid therapy are well known in the art, as are the techniques for the creation of transgenic organisms[35]. For example, pigs and goats can be used as potential transgenic animals producing the GM-CSF and IL-15 protein conjugate. In a preferred embodiment pigs are used in view of the fact that they possess high homology to humans in terms of MHC molecules and they are considered as a potential source of tissue and organs, in particular pancreas, heart, kidney and cornea amongst others.

It is to be understood that the administration of GM-CSF and IL-15 protein conjugate nucleic acid in gene therapy may take several forms, all of which are included in the scope of the present invention. The nucleic acid encoding GM-CSF and IL-15 protein conjugate may be administered in such a manner as to add the GM-CSF and IL-15 protein conjugate nucleic acid to the genome of the cell or the organism. For example, administering a nucleic acid encoding GM-CSF and IL-15 protein conjugate, under the control of a promoter which results in an increase expression of GM-CSF and IL-15 protein conjugate, results in the incorporation of the nucleic acid into the genome of the cell or the organism, such that increased levels of GM-CSF and IL-15 protein conjugate are made. For example, this may be done to a cell population which is susceptible to undergo an undesirable level of programmed cell death, to preserve the cells.

Construction of appropriate expression vehicles and vectors for therapeutic applications will depend on the organism to be treated and the purpose of the gene therapy. The selection of appropriate promoters and other regulatory DNA will proceed according to known principles, based on a variety of known gene therapy techniques. For example, retroviral mediated gene transfer is a very effective method for therapy, as systems utilizing packaging defective viruses allow the production of recombinants which are infectious only once, thus avoiding the introduction of wild-type virus into an organism. Alternative methodologies for therapy include non-viral transfer methods, such as calcium phosphate co-precipitation, mechanical techniques, for example microinjection, membrane fusion-mediated transfer via liposomes, as well as direct DNA uptake and receptor-mediated DNA transfer.

C. Compositions

The invention also includes pharmaceutical compositions containing GM-CSF and IL-15 conjugate proteins or nucleic acids for use in immune suppression, inducing angiogenesis, and inhibiting cell death.

Such pharmaceutical compositions can be for intralesional, intravenous, topical, rectal, parenteral, local, inhalant or subcutaneous, intradermal, intramuscular, intrathecal, transperitoneal, oral, and intracerebral use. The composition can be in liquid, solid or semisolid form, for example pills, tablets, creams, gelatin capsules, capsules, suppositories, soft gelatin capsules, gels, membranes, tubelets, solutions or suspensions.

The pharmaceutical compositions of the invention can be intended for administration to humans or animals or cells or tissue in culture. Dosages to be administered depend on individual needs, on the desired effect and on the chosen route of administration.

The pharmaceutical compositions can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985).

On this basis, the pharmaceutical compositions include, albeit not exclusively, the active compound or substance in association with one or more pharmaceutically acceptable vehicles or diluents, and contained in buffered solutions with a suitable pH and iso-osmotic with the physiological fluids. The pharmaceutical compositions may additionally contain other agents such as immunosuppressive drugs or antibodies to enhance immune tolerance.

In one embodiment, the pharmaceutical composition comprises an effective amount of a GM-CSF and IL-15 conjugate protein in admixture with a pharmaceutically acceptable diluent or carrier.

In another embodiment, the pharmaceutical composition comprises an effective amount of a nucleic acid molecule encoding a GM-CSF and IL-15 conjugate protein in admixture with a pharmaceutically acceptable diluent or carrier.

D. Screening Assay

As mentioned previously, the GM-CSF and IL-15 conjugate exerts it effect through the binding of the IL-15 portion of the conjugate to the IL-15 receptor (IL-15R). In particular, the inventors have demonstrated that the GM-CSF and IL-15 fusion protein substantially increased the β chain-dependent phosphorylation of STAT3 and suppressed the γ chain-dependent phosphorylation of STAT5 (FIG. 11c). The identification of the mechanism by which the conjugate exerts its effects allows the development of screening assays that could be used to test other compound for immune suppressive activity.

Accordingly, the present invention also provides a screening assay for determining whether or not a compound is an immune suppressant comprising a) incubating the compound with cells that express the IL-15 receptor; and b) determining the effect of the compound on the phosphorylation of STAT3 in the cells wherein an increase in phosphorylation as compared to a control indicates that the compound may be an immune suppressant.

The test compound can be any compound which one wishes to test including, but not limited to, proteins, peptides, nucleic acids (including RNA, DNA, antisense oligonucleotide, peptide nucleic acids), carbohydrates, organic compounds, small molecules, natural products, library extracts, bodily fluids and other samples that one wishes to test for immune suppressive activity.

In one embodiment, the test compound is a protein conjugate comprising an IL-15 receptor ligand.

The present invention also provides a screening assay for determining whether or not a conjugate comprising an IL-15 receptor ligand is an immune suppressant comprising a) incubating the conjugate with cells that express the IL-15 receptor; and b) determining the effect of the conjugate on the phosphorylation of STAT3 in the cells wherein an increase in phosphorylation as compared to a control indicates that the conjugate may be an immune suppressant.

The conjugate to be tested can be any conjugate that contains an IL-15R ligand, i.e. a protein that can bind to IL-15R. The conjugate will preferably be a fusion protein that comprises a first protein linked to a second protein that binds to the IL-15R. The second protein is preferably IL-15 or a fragment, analog or homolog thereof. The first protein can be any protein which one wants to test for its ability to impact the activity of an IL-15R ligand such as IL-15.

The control can be any suitable control including a fusion protein that does not contain an IL-15R ligand. The control can also be IL-15 alone that is not in a fusion protein.

The cells can be any cells that either naturally express IL-15R or are transduced or transfected to express IL-15R.

STAT-3 phosphorylation can be determined using techniques known in the art including immunoblotting with antibodies to phosphorylated STAT3 as described in the Examples.

Once it has been determined that a test compound or conjugate does increase the phosphorylation of STAT-3, it can be further tested for immune suppressive activity using techniques known in the art including the assays described herein for the GM-CSF and IL-15 conjugate.

The screening methods of the invention include high-throughput screening applications. For example, a high-throughput screening assay may be used which comprises any of the methods according to the invention wherein aliquots of cells transfected with a IL-15 receptor are exposed to a plurality of test compounds within different wells of a multi-well plate. Further, a high-throughput screening assay according to the invention involves aliquots of transfected cells which are exposed to a plurality of candidate conjugates in a miniaturized assay system of any kind. Another embodiment of a high-throughput screening assay could involve exposing a transduced cell population simultaneously to a plurality of test compounds.

The method of the invention may be "miniaturized" in an assay system through any acceptable method of miniaturization, including but not limited to multi-well plates, such as 24, 48, 96 or 384-wells per plate, micro-chips or slides. The assay may be reduced in size to be conducted on a micro-chip support, advantageously involving smaller amounts of reagent and other materials. Any miniaturization of the process which is conducive to high-throughput screening is within the scope of the invention.

EXAMPLES

Methods

Animals, Cell Lines, Recombinant Proteins, Antibodies, and ELISA Kits.

All female mice used for experimentations were 6-8 weeks old. The WT C57Bl/6 mice, $CD4^{-/-}$, $CD8^{-/-}$, or beige mice were purchased from the Jackson Laboratory (Bar Harbor, Me.). The C57Bl/6-derived B16F0 and human U87GM cell lines were generously provided by M. A. Alaoui-Jamali and S. Richard respectively (Lady Davis Institute, Montreal, Qc, CANADA) and cultured in DMEM (Wisent Technologies, Rocklin, Calif.) supplemented with 10% FBS (Wisent Technologies) and 50 U/ml of Pen/Strep (Wisent Technologies). The cell lines JAWSII and CTLL2 were purchased from American Type Culture collections (Manassas, Va.) and grown according to manufacturer's recommendations. Recombinant proteins (IL-15/IL-15Rα-Fc/GM-CSF) and antibodies against rIL-15 or rGM-CSF were purchased form R&D systems (Minneapolis, Minn.). Antibodies against vWF and α-tubulin were purchased from Santa Cruz Biotechnology (Santa Cruz, Calif.). Polyclonal antisera directed against phosphorylated STAT3, phosphorylated STAT5, STAT3, STAT5 or Bcl-XL were purchased from Cell Signalling Technology (Danvers, Mass.). Anti-mouse Fcγ III/II, CD3, CD4, CD8, NK1.1 or isotype control antibodies used in flow cytometry were purchased from BD Biosciences (San Diego, Calif.). The ELISA kits for mIFN-γ, mIL-10 or mIL-15 were purchased from BD Biosciences and R&D systems, respectively.

Vector Construct and Protein Modeling.

The cDNAs for mIL-15 and GM-CSF were obtained from Invivogen (San-Diego, Calif.) were cloned into the bicistronic $AP^2$ retrovector in frame allowing the expression of both the chimeric transgene and $GFP^4$. For the human homolog of GIFT15, the cDNAs for hIL-15 and GM-CSF (Invivogen) were cloned in frame in the PCMV mammalian expression vector. To build a structural model of mGIFT15 by homology modeling, crystal structures of human GM-CSF and human IL2 (D chain) were used as the templates for mouse GM-CSF and mouse IL-15, respectively. The structural template for the region connecting GM-CSF and IL-15 was identified by fold recognition methods, using software PROSPECT v2 (Oak Ridge National Laboratory, Oak Ridge, Tenn.). Based on the templates identified, 50 structural models of GIFT15 were generated using software MODELLER v6 (University of California at San Francisco). The structural model with lowest objective function was selected for further analysis. Both of the stereochemical quality and packing quality of the GIFT15 model were evaluated to be excellent using software WHAT IF v4.99 (Radboud University Nijmegen, Netherlands). Next, a structural model of mGIFT15 in complex with cytokine receptor was generated based on crystal structure of the IL2 signaling complex, which is the trimeric assembly of IL2Rα, IL2Rβ and IL2Rγ in complex with IL2. Since IL-15 and IL2 share the IL2Rβ and IL2Rγ for signal transduction but each use different a chain, crystal structure of IL-15Rα was used as an additional template. Specifically, the IL-15 portion of mGIFT15 was aligned with the IL2 in the IL2 signaling complex over the secondary structures. The IL2Rα consists of two sushi domains but the ligand binding is mediated primarily by the N-terminal sushi domain (IL2Rα D1), whereas the IL-15Rα contains only one. Therefore, the inventors aligned the IL-15Rα over the IL2Rα D1 domain to generate a model of GIFT15 in complex with IL-15Rα, IL2Rβ and IL2Rγ.

Transgene Expression and Proliferation Assays.

The GIFT15 encoding retroviral plasmid was introduced into the 293-GP2 packaging cell (Clontech, Mountain View, Calif.) following manufacturer's instructions and concentrated retroparticles were used to genetically modify B16F0 melanoma cells. The supernatant from the polyclonal population was tested by western blot. To test the bioactivity of GIFT15, the CTLL-2 or JAWSII cell lines were plated at a density of $10^5$ cells/well in a 96-well plate with increasing concentrations of cytokines. The cells were incubated for 72 hours, and 20 μL of 3-(4,5-dimethylhiazol-2-yl)-2,5-diphenyltetrazolium bromide (MTT) solution was added for 4 hours of incubation at 37° C. and read at an absorbance of 570 nm. For hGIFT15, Chinese Hamster Ovary (CHO) cells have been stably transfected to express the protein, which was confirmed by Western Blot.

Murine B16F0 Tumor Implantation in Syngeneic C57Bl/6 Mice & Immune Infiltrate Analysis One million cytokine-secreting B16F0 cells were injected subcutaneously (n=6 per group) in immunocompetent C57Bl/6 mice, and tumor growth was monitored over time. All implanted B16F0 polyclonal populations produced comparable molar quantities of cytokines (0.6±0.1 pmol per $10^6$ cells every 24 hours). For immune infiltrate analysis, one million cytokine-secreting B16F0 cells were mixed with 500 μL of Matrigel™ (BD Biosciences) at 4° C. and injected subcutaneously in C57bl/6 mice (n=6 per group). Implants were surgically removed two weeks post-transplantations and digested are reported previously[4]. After incubation with anti-Fcγ III/II mAb for 1 hour, cells were incubated for 1 hour at 4° C. with anti-mouse CD3, CD4, CD8 and NK1.1, or proper isotypic controls. Labelled cells were subsequently analyzed by flow cytometry with a Becton-Dickinson FACScan.

Murine B16F0 Tumor Implantation in NOD-SCID Mice and vWF Immunostaining.

One million GIFT15-secreting or GFP-expressing B16F0 cells were injected subcutaneously (n=5 per group) in immunocompromised NOD-SCID mice, and tumor growth was monitored over time. For vWF immunostaining, animals were sacrificed and tumors retrieved for paraffin embedment before being cut and probed with an anti-vWF antibody as reported elsewhere[36]. Total number of blood vessels was counted and divided by the total surface area calculated using Scion image software (Scion Corporation, MA, USA) in order to obtain blood vessel density.

Surface Plasmon Resonance (SPR)

mGIFT15 was purified by immunoaffinity column packed using CNBr-sepharose (Amersham, N.J., USA) according to manufacturer's instructions. The binding interaction between mGIFT15 and rmIL-15Rα-Fc was examined in real-time using a BIACORE 3000 with research-grade CM5 sensor chips (Biacore AB, Uppsala, Sweden). Based on the manufacturer's recommendations, active CM5 surfaces were prepared by immobilizing rIL-15Rα-Fc (10 μg/mL in 10 mM sodium acetate pH 5.0) using the Amine Coupling Kit (Biacore AB) and HBS-M running buffer. Corresponding reference surfaces were prepared in the similar manner in the absence of any ligand. As a positive control, rIL-15 was injected at 50 μL/min (180 sec association+180 sec dissociation) over the reference and amine-coupled rIL-15Rα-Fc surfaces (1300 RU). Regeneration was achieved using two 30 second pulses of HBS-M containing 0.5 M NaCl, 50 mM EDTA, and 0.05% (v/v) TritonX-100 or Empigen. For the test sample, purified mGIFT15 was injected over the same sensor chip surfaces and regenerated in an identical manner. All binding data presented were "double-referenced" and analyzed according to a 1:1 interaction model using BIAevaluation 4.1 (Biacore AB).

GIFT15-Mediated Biochemical Responses

Media from GFP transduced B16 cancer cells or inoculated with 30 μM of rmIL-15, rmGM-CSF, both cytokines together or mGIFT15 was used to stimulate unfractionated $10^6$ splenocytes for 15 minutes before being lysed and loaded on a 4-20% gradient gel and probed with anti phosphorylated STAT3 or STAT5 rabbit antisera. Total STAT3 or STAT5 proteins were used as loading controls for the immunoblotting. For apoptosis assays, $10^6$ splenocytes were cultured using the same conditions as before for 36 hrs before being stained for PI and annexin-V. The same experiment was repeated to analyse Bcl-XL protein expression by immunoblotting on cell lysate. For the splenocyte proliferation assay, $10^5$ splenocytes were cultured with increasing concentrations of cytokines for 72 hrs at 37° C. The reaction was read at 570 nm after adding 20 μl of MTT reagent for 4 hours at 37° C.

Induction of IFN-γ and 2-Way MLR Reaction

The supernatant of $10^5$ splenocytes stimulated for 36 hrs with equimolar concentrations of cytokines was centrifuged and used to detect IFN-γ secretion by ELISA. For the MLR assay, 1.5×$10^5$ splenocytes of BALB/c and C57Bl/6 mice or 1.5×$10^5$ PBLs were mixed or treated separately with mGIFT15 or hGIFT15, respectively and all cells were incubated at 37° C. for a period of 72 hrs before collecting the supernatant to detect IFN-γ by ELISA.

Allogeneic B16F0 and Xenogeneic U87GM Transplantations

Allogeneic transplantations were performed by injecting $10^7$ live B16-GFP or B16-GIFT15 in immunocompetent BALB/c mice (n=10) and tumor growth was followed over time. For spleen analysis, animals with GIFT15 tumors exceeding 1,000 mm³ or with the largest B16-GFP tumors were sacrificed and their spleen removed and weighed. Paraffin-embedded slides were also prepared for Hematoxylin and Eosin (H&E) staining. For flow cytometry analysis, the spleens were digested to obtain a single cell suspension that was then stained using antibodies against mouse CD3, CD4, CD8, CD25, and NK1.1. For xenotransplantation, $10^7$ live U87-GFP or U87-GIFT15 (polyclonal populations) transduced as explained previously were injected subcutaneously to monitor tumor growth and graft survival over time. The same experiment was performed in WT C57Bl/6 mice (n=6), CD4$^{-/-}$ (n=10), CD8$^{-/-}$ (n=10), or in beige mice (NK deficiency; n=10).

Macrophage Migration Assays and Signalling

Murine peritoneal macrophages isolated from C57bl/6 mice by lavage of the abdominal cavity with RPMI were consistently >85% Mac-3 positive by FACS. After isolation and plating for the removal of non-adherent cells, $10^5$ cells per well were plated in the top chamber of a 0.15% gelatin-coated 50-μm Transwell plate. The lower chambers were filled in triplicates with 500 μL of serum-free RPMI with 0.1 or 1 nmol/L of GFP CM containing rIL-15, rGM-CSF, both cytokines or GIFT15 supernatants. After 18 hours of incubation at 37° C., the top chambers were removed, thoroughly washed, removed from cells on the top filter with a cotton swab, fixed in methanol, and stained with violet blue dye. The cells on the bottom filter of 10 high power fields (×400) were counted for each well.

For signalling analysis, mGIFT15 was purified by immunoaffinity column packed using CNBr-sepharose (Amersham, N.J., USA) according to manufacturer's instructions. To stimulate peritoneal macrophages, JAWSII cells and splenocytes, 30 pmols of rmIL-15, rmGM-CSF, both cytokines together or mGIFT15 were added to $10^6$ cells for 15 minutes before being lysed and loaded on a 4-20% gradient gel and probed with rabbit anti-phosphorylated STAT3 or STAT5. Total STAT3 or STAT5 proteins were used as loading controls for the immunoblotting. To investigate STAT3 and STAT5 signalling in human cells, $10^6$ Peripheral Blood Mononuclear Cells (PBMCs) were stimulated for 15 minutes with 30 pmols of rhIL-15, rhGM-CSF added to the supernatant of GFP transduced CHO cells. hGIFT15 was derived from the supernatant of CHO transduced with hGIFT15 cDNA.

Angiogenic Protein Arrays and Secreted Factors

Murine peritoneal macrophages isolated from C57BI/6 mice as shown previously were cultured with 30 pmols of cytokines (serum-free media) for 72 hrs at 37° C., and supernatants were then re-collected, filtered through a 0.45 μm filter before being screened using the angiogenic protein arrays according to manufactures instructions. The detected protein (TIMP-2) was then confirmed by western blot. Gelatin zymography was used to assess the extent of MMP-2 activity. Briefly, an aliquot (20 μl) of the culture medium was subjected to SDS-PAGE in gels containing 0.1 mg/ml gelatin. The gels were then incubated in 2.5% Triton X-100 and rinsed in nanopure distilled $H_2O$. Gels were further incubated at 37° C. for 20 hrs in 20 mM NaCl, 5 mM $CaCl_2$, 0.02% Brij-35, 50 mM Tris-HCl buffer, pH 7.6, then stained with 0.1% Coomassie Brilliant blue R-250 and destained in 10% acetic acid, 30% methanol in $H_2O$. Gelatinolytic activity was detected as unstained bands on a blue background. The same culture medium was used in a western blot in order to confirm the presence of MMP2 as well as for MMP9 at the protein level. Supernatants were also used to detect the presence of VEGF and TGF-β ELISAs according to manufacturers instructions.

Human monocytes were cultured for 48 hrs in the presence of hGIFT15 (30 pmols) derived from hGIFT15 transduced CHO cells, their supernatant was collected, filtered with a 0.45 μm filter and subsequently screened in both, the angiogenic and generic, cytokine protein arrays according to manufacturers' instructions.

Cellular Phenotype after mGIFT15 Treatment In Vitro

Splenocytes collected from C57BI/6 mice were cultured with mGIFT15 (30 pmols) for 8 days. After incubation with anti-Fcγ III/II mAb for 1 hour, cells were incubated for 1 hour at 4° C. with anti-mouse MHCI/II, CD2, CD19, CD3, CD4, CD8, NK1.1, CD11b, Gr1, FasL, B7H1, CD80, CD86 or the appropriate isotypic controls. Labelled cells were subsequently analyzed by flow cytometry with a Becton-Dickinson FACScan. In addition, cells were labeled using CFSE (Invitrogen) according to manufacturer's instructions, and analyzed by flow cytometry for CFSE positive cells over 4 days. Unlabelled cells were used as control for appropriate gating and settings for flow cytometry Indirect Effects of mGIFT15 on MLRs mGIFT15 pre-treated C57BI/6 splenocytes (GT-B6) were added in a 1:1 ratio to naïve BALB/c splenocytes. 72 hrs later, the supernatant was collected to analyse IFN-γ by ELISA. The same experiment was repeated with both, C57BI/6 and BALB/c, splenocyte populations were pre-treated with cytokines.

mGIFT15 Treated Splenocytes and Antigen Presentation

Due to the high expression level of MHCII on GT-B6, an antigen presentation assay was performed using the experimental antigen rOVA. Briefly, cytokine-treated C57BI/6 splenocytes as shown previously were incubated for 24 hrs in the presence of rOVA at 37° C. before being added in a 1:1 ratio hybridoma class II cell line responding to OVA peptides presented by MHCII (panel A) or to primary OTII-derived T-cells (panel B). 72 hrs later, the supernatants were collected and tested for IFN-γ by ELISA.

mGIFT15 Treated Splenocytes and Syngeneic Cellular Inhibition

To test for the inhibitory ability of GT-B6 as third party cell in an antigen activation assay the following experiment has been performed. Peritoneal C57BI/6 macrophages were plated for 24 hrs then non-adherent cells were removed by washing. rOVA (1 mg/ml) was added for another 24 hrs. After washing for unprocessed antigen, primary OTII-derived T-cells were added in a 1:1 ratio to GT-B6 for a total of 72 hrs. The supernatant was then collected and tested for IFN-γ by ELISA as a read-out for antigen activation. In order to identify the cell targeted by GT-B6, macrophages presenting the OVA peptide were fixed using 1% paraformaldehyde for 20 min at RT then the same assay was performed as explained previously. IFN-γ was again used as a read-out system. As a disease model for cellular inhibition in vitro, EAE-specific T-cells collected from EAE mice were used following the same procedure as with OTII-derived T-cells assay.

In Vivo Analysis of EAE Mice after Injection with GIFT15 Treated Splenocytes

Purified synthetic MOG$_{35-55}$ peptide (1 mg/ml) was emulsified in a 1:1 volume ratio in Complete Freund's Adjuvant containing 4 mg/ml *Mycobacterium tuberculosis* H35RA, and the mixture was injected subcutaneously at the base of the tail (50 μl/side containing 25 μg MOG, 100 μg *M. tuberculosis* H35RA). In addition, animals received pertussis toxin immediately after the sc injection (300 ng in 0.2 ml saline for a 20 g mouse, eg. 0.015 mg/kg) by IP injection, repeated two days later. Animals were monitored by assigning a disease score (0-5). Once at score 2, mice received 3 IV injections of GIFT15-treated C57BI/6 splenocytes ($6 \times 10^6$ cells/injection).

Identification of Inhibitory Soluble Factors Secreted by mGIFT15 Treated Splenocytes To identify any soluble factor that might be involved in the inhibition process induced by GT-B6, CM from splenocytes treated previously for 4 days with the different cytokine conditions was collected and added directly on peritoneal C57BI/6 macrophages presenting OVA peptide to syngeneic OTII-derived T-cells. 72 hrs later, the supernatants were collected and tested for the IFN-γ by ELISA as a read-out for activation.

ELISA for IL10 was also performed on the collected CM. Once identified, neutralizing anti-IL10 were added to the CM collected from GT-B6 before adding it to macrophages presenting the OVA peptide. IFN-γ was again used as a marker of activation by ELISA testing.

mGIFT15 Treated Splenocytes can Block Humoral Responses In Vivo

The inhibitory effect of GT-B6 was tested directly in vivo using mice immunized with rOVA. Briefly, C57BI/6 mice (n=5/group) were injected IP with 1 μg of rOVA. One week later, sera from immunized mice was tested for their anti-OVA titer. Once confirmed, $10^7$ GT-B6 were injected IP and blood was collected weekly for anti-OVA IgM and IgG analysis. In order to know if the titer decrease in mice that have received the cellular therapy is due to a transient immunosuppression rather then tolerance, the positive control group (rOVA immunization only) was left until the anti-OVA titer went to baseline and all groups were re-challenged with 1 ug rOVA. Both IgG and IgM anti-OVA antibodies were then screened by ELISA coated with rOVA.

mGIFT15 Treated Splenocytes and Allogeneic Cellular Inhibition

To test for the inhibitory ability of mGIFT15 treated splenocytes as third party cell in an allogeneic activation assay, peritoneal C57BI/6 macrophages were plated for 24 hrs then non-adherent cells were removed by washing. BALB/c splenocytes were added in different ratios to mGIFT15 pre-treated BALB/c splenocytes for a total of 72 hrs. CM collected for the different cytokine treatments were also added to the allogeneic stimulation in vitro to demonstrate the inhibitory activity of a soluble factor secreting following mGIFT15 treatment.

Statistical Analysis

P values were calculated by paired Student t-test.

Accession Codes

PBD entries for the crystal structures of GM-CSF (2 gmf); human IL2 (1erj); region connecting GM-CSF and IL-15 (1orc); IL2 signalling complex (1erj); and IL-15Rα (2ers).

While the invention has been described in connection with specific embodiments thereof, it will be understood that it is capable of further modifications and this application is intended to cover any variations, uses, or adaptations of the invention following, in general, the principles of the invention and including such departures from the present disclosures as come within known or customary practice within the art to which the invention pertains and as may be applied to the essential features herein before set forth, and as follows in the scope of the appended claims.

REFERENCES

1. Dranoff G, Jaffee E, Lazenby A, Golumbek P, Levitsky H, Brose K, Jackson V, Hamada H, Pardoll D, Mulligan R C. Vaccination with irradiated tumor cells engineered to secrete murine granulocyte-macrophage colony-stimulating factor stimulates potent, specific, and long-lasting anti-tumor immunity. *Proceedings of the National Academy of Sciences*. 90: 3539-43 (1993).
2. Irvine K R, Rao J B, Rosenberg S A, Restifo N P. Cytokine enhancement of DNA immunization leads to effective treatment of established pulmonary metastases. *Journal of Immunology*. 156: 238-45 (1996).
3. Gillies S D, Lan Y, Brunkhorst B, Wong W K, Li Y, Lo K M Bi-functional cytokine fusion proteins for gene therapy and antibody-targeted treatment of cancer. *Cancer Immunology Immunotherapy*. 51: 449-460 (2002).
4. Stagg J, Wu J H, Bougamin N, Galipeau J. Granulocyte-macrophage colony stimulating factor and interleukin-2 fusion cDNA for cancer gene therapy. *Cancer Research*. 64: 8795-99 (2004).
5. Demetri G D, Griffin J D. Granulocyte colony-stimulating factor and its receptor. *Blood.*; 78: 2791-808 (1991).
6. Diab A, Cohen A D, Alpdogan O, Perales M A. IL-15: targeting CD8+ T cells for immunotherapy. *Cytotherapy*. 7:23-35 (2005).
7. McInnes I B, Gracie J A. Interleukin-15: a new cytokine target for the treatment of inflammatory diseases. *Curr Opin Pharmacol*. 4:392-7. (2004).
8. Ferrari-Lacraz S, Zheng X X, Kim Y S, Li Y, Maslinski W, Li X C, Strom T B. An antagonist IL-15/Fc protein prevents costimulation blockade-resistant rejection. *J Immunol* 167: 3478-85 (2001).
9. Zheng X X, Gao W, Donskoy E, Neuberg M, Ruediger M, Strom T B, Moll T. An antagonist mutant IL-15/Fc promotes transplant tolerance. *Transplantation*. 81:109-16 (2006).
10. Waldmann T A. The biology of interleukin-2 and interleukin-15: implications for cancer therapy and vaccine design. *Nature Reviews Immunology* 6, 595-601 (2006).
11. Waldmann T A, Tagaya Y. The multifaced regulation of interleukin-15 expression and the role of this cytokine in NK cell differentiation and host response to intracellular pathogens. *Annual Reviews in Immunology*. 17: 19-49 (1999).
12. Tagaya Y, Bamford R N, DeFilippis A P, Waldmann T A. IL-15: a pleiotropic cytokine with diverse receptor/signalling pathways whose expression in controlled at multiple levels. *Immunity*. 4: 329-36 (1996).
13. Mrozek E., Anderson P, Caliguiri M A. Role of interleukin-15 in the development of $CD56^+$ natural killer cells from $CD34^+$ hematopoietic progenitor cells. *Blood*. 87: 2632-40 (1996).
14. Ohteki T, Yoshida H, Matsuyama T, Duncan G S, Mak T W, Ohashi P S. The transcription factor interferon regulatory factor 1 (IRF-1) is important during the maturation of natural killer $1.1^+$ T-cell receptor-alpha/beta+(NK1+T) cells, natural killer cells, and intestinal intraepithelial T cells. *Journal of Experimental Medicine*. 187: 967-72 (1998).
15. Mossman T R, Coffman R L. Heterogeneity of cytokine secretion patterns and functions of helper T cells. *Advances in Immunology*. 46: 111-47 (1989).
16. Uleft G C, Ketheesan N, Hirst R G. Cytokine gene expression in innately susceptible BALB/c mice and relatively resistant C57BI/6 mice during infection with virulent *Burkholderia pseudomallei. Infection and Immunity*. 68: 2034-42 (2000).
17. Wahl S. M., Wen J., Moutsopoulos N M. The kiss of death: interrupted by NK-cell close encounters of another kind. *Trends in Immunology*. 4: 161-4 (2006).
18. Barnden M. J., Allison J., Heath W R, Carbone F R. Defective TCR expression in transgenic mice constructed using cDNA-based α- and β-chain genes under the control of heterologous regulatory elements. *Immunology and Cell Biology* 76: 34-40 (1998).
19. Lorenzen I, Dingley A J, Jacques Y, Grotzinger J. The Structure of the Interleukin-15α Receptor and Its Implications for Ligand Binding. *Journal of Biological Chemistry*. 281: 6642-6647 (2006).
20. Jérôme Bernard, et al. Identification of an Interleukin-15α Receptor-binding Site on Human Interleukin-15. *Journal of Biological Chemistry*. 279: 24313-22, (2004).

21. Stauber D J, Debler E W, Horton P A, Smith K A, Wilson I A. Crystal structure of the IL-2 signaling complex: Paradigm for a heterotrimeric cytokine receptor. *Proceeding National Academy of Science.* 103: 2788-2793 (2006).
22. Sainathan S K, Tu L, Bishnupuri K S, Han M, Li A, Newberry R D, McDonald K G, Crimmins D L, Houchen C, Anant S, Dieckgraefe B K. PEGylated murine Granulocyte-macrophage colony-stimulating factor: production, purification, and characterization. *Protein Expression & Purification.* 44: 94-103 (2005).
23. Burgess A W, Metcalf D. Serum half-life and organ distribution of radiolabeled colony stimulating factor in mice. *Experimental Hematology.* 5: 456-64 (1977).
24. Pettit D K, Bonnert T P, Eisenman J, Srinivasan S, Paxton R, Beers C, Lynch D, Miller B, Yost J, Grabstein K H, Gombotz W R. Structure-function studies of interleukin 15 using site-specific mutagenesis, polyethylene glycol conjugation, and homology modeling. *Journal of Biological Chemistry.* 272: 2312-8 (1997).
25. Giron-Michel J, Caignard A, Fogli M, Brouty-Boyé D, Briard D, van Dijk M, Meazza R, Ferrini S, Lebousse-Kerdilès C, Clay D, Bompais H, Chouaib S, Péault B, Azzarone B. Differential STAT3, STAT5, and NF-kappaB activation in human hematopoietic progenitors by endogenous interleukin-15: implications in the expression of functional molecules. *Blood.* 102: 109-17 (2002).
26. Kisselva T., Bhattacharya S., Braunstein J., Schindler C W. Signaling through the JAK/STAT pathway, recent advances and future challenges. *Gene.* 285: 1-24 (2002).
27. Bromberg J., Darnell J E. The role of STATs in transcriptional control and their impact on cellular function. *Oncogene.* 19: 2468-73 (2000).
28. Smithgall T E, Briggs S D, Schreiner S, Lerner E C, Cheng H, Wilson M B. Control of myeloid differentiation and survival by Stats. *Oncogene.* 19: 2612-2618 (2000).
29. Catlett-Falcone R, Landowski T H, Oshiro M M, Turkson J, Levitzki A, Savino R, Ciliberto G, Moscinski L, Fernandez-Luna J L, Nunez G, Dalton W S, Jove R. Constitutive activation of STAT3 signaling confers resistance to apoptosis in human U266 myeloma cells. *Immunity.* 10: 105-15 (1999).
30. Niu G, Bowman T, Huang M, Shivers S, Reintgen D, Daud A, Chang A, Kraker A, Jove R, Yu H. Roles of activated Src and STAT3 signaling in melanoma tumor cell growth. Oncogene. 21: 7001-10 (2002).
31. Angiolillo A L, Kanegane H, Sgadari C, Reaman G H, Tosato G. Interleukin-15 promotes angiogenesis in vivo. *Biochemical Biophysical Research Communication.* 233: 231-7 (1997).
32. Estess P, Nandi A, Mohamadzadeh M, Siegelman M H. Interleukin 15 induces endothelial hyaluronan expression in vitro and promotes activated T cell extravasation through a CD44-dependent pathway in vivo. *Journal of Experimental Medicine.* 190: 9-19 (1999).
33. Egebad M, and Werb Z. New Functions For the Matrix Metalloproteinases in Cancer Progression. *Nat Rev Cancer* 2: 161-174 (2002)
34. Itoh T, Tanioka M, Yoshida H, Yoshioka T, Nishimoto H, Itohara S. Reduced angiogenesis and tumor progression in gelatinase A-deficient mice. *Cancer Res.* 58:1048-51 (1998).
35. Carl A. Pinkert. Transgenic Animal Technology: A Laboratory Handbook. Academic Press; 1st edition (1994).
36. Perri S R, Martineau D, Francois M, Lejeune L, Bisson L, Durocher Y, Galipeau J. Plasminogen kringle 5-engineered glioma cells block migration of tumor-associated macrophages and suppress tumor vascularization and progression. *Cancer Research.* 65: 8359-65 (2005).

The invention claimed is:

1. A method of inhibiting graft rejection of a transplanted cell comprising administering an effective amount of a GM-CSF and IL-15 conjugate protein comprising the sequence shown in SEQ ID NO:2 or 4 to an animal in need thereof.

2. The method according to claim 1 wherein said cell is a xenogeneic cell.

3. The method according to claim 1 wherein said cell is an allogeneic cell.

* * * * *